(12) United States Patent
Duan et al.

(10) Patent No.: US 8,361,792 B2
(45) Date of Patent: Jan. 29, 2013

(54) RANDOM HOMOZYGOUS GENE PERTURBATION TO ENHANCE ANTIBODY PRODUCTION

(75) Inventors: Roxanne Duan, Bethesda, MD (US); Michael Goldblatt, McLean, VA (US)

(73) Assignee: Functional Genetics, Inc., Gaithersburg, MD (US)

( * ) Notice: Subject to any disclaimer, the term of this patent is extended or adjusted under 35 U.S.C. 154(b) by 253 days.

(21) Appl. No.: 12/777,417

(22) Filed: May 11, 2010

(65) Prior Publication Data

US 2011/0027878 A1 Feb. 3, 2011

Related U.S. Application Data

(63) Continuation of application No. 11/928,393, filed on Oct. 30, 2007, now Pat. No. 7,745,148.

(60) Provisional application No. 60/855,127, filed on Oct. 30, 2006.

(51) Int. Cl.
*C12N 5/07* (2010.01)
(52) U.S. Cl. .................................................. 435/327
(58) Field of Classification Search .................. None
See application file for complete search history.

(56) References Cited

U.S. PATENT DOCUMENTS

| | | | |
|---|---|---|---|
| 4,816,567 A | 3/1989 | Cabilly et al. | |
| 5,981,214 A | 11/1999 | Skoultchi | |
| 6,054,561 A | 4/2000 | Ring | |
| 7,479,379 B2 * | 1/2009 | Rycyzyn et al. | 435/69.1 |
| 2006/0240021 A1 | 10/2006 | Li et al. | |

OTHER PUBLICATIONS

U.S. Appl. No. 60/855,127, filed Oct. 30, 2006, Duan.
Kohler, et al., "Continuous Cultures of Fused Cells Secreting Antibody of Predefined Specificity", Nature, 256, 495-497 (1975).
Li, et al., "tsg101: A Novel Tumor Susceptiblity Gene Isolated by Controlled Homozygous Functional Knockout of Allelic Loci in Mammalian Cells", Cell, vol. 85, 319-329, (1996).
Gumienny, et al., "CED-12/ELMO, a Novel Member of the Crkll/Dock180/Rac Patheway, Is Required for Phagocytosis and Cell Migration", Cell, vol. 107, 27-41, (2001).

* cited by examiner

*Primary Examiner* — Sean Aeder
(74) *Attorney, Agent, or Firm* — Steven B. Kelber; Berenato & White, LLC

(57) ABSTRACT

The invention reflects enhanced antibody expression of an antibody of interest by cell lines transformed by random homozygous gene perturbation methods to either increase or decrease the expression pattern of a gene of the cell line other than the antibody of interest. The transformed cell line exhibits specific productivity rates, SPR, for the RHGP transformed cell liens of 1.5 or more, as compared with the antibody expressing cell line parents prior to transformation by RHGP. A knock out or anti-sense construct may be devised to reduce expression of the target gene, a promoter may be inserter to enhance expression of the target gene. The antibodies expressed by the transformed cell lines exhibit the binding properties of their parent cell lines prior to transformation with RHGP, and increase Total Volumetric Production of said antibody by said cells in a given volume.

6 Claims, 19 Drawing Sheets

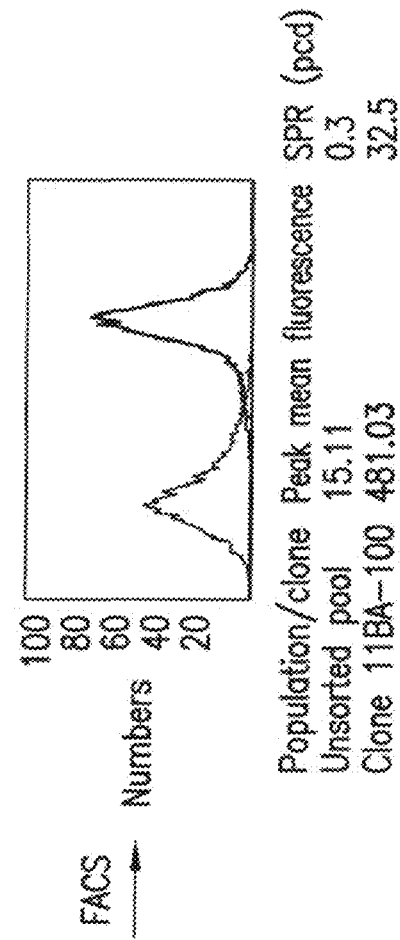
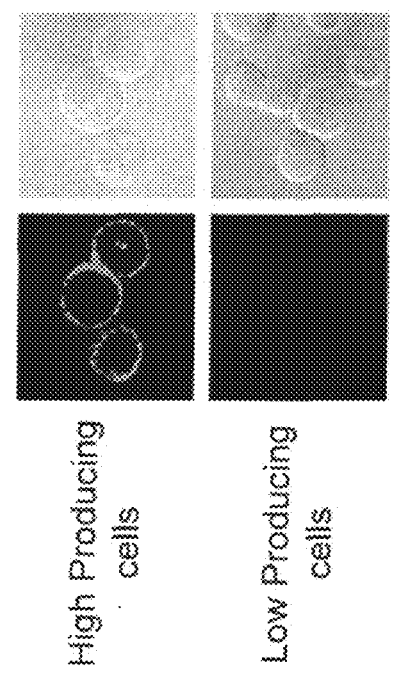
FIG. 3

ELMO1

First RNAi Gene Identified from High Specific Productivity Clones

SEQ ID NOS: 5, 6, 7, 8

Sequence View: Difference Format. Color behind non-matches

Human ELMO1    1  mppadivkvatewpgypklmatdakkolsatikevcdgwslartkeyfalqhdssntyitekmneikngtlrltspagnagplne
Mouse ELMO1    1
Rat ELMO1      1
CHO-ELMO1      1

Human ELMO1   91  rigessmdakisalikdlaelsrdvtfageinlqqistltqwvesteryqlqkimocfgdmisfsltafvelmdtqswdfsvaf
Mouse ELMO1   91
Rat ELMO1     91
CHO-ELMO1     91

Human ELMO1  181  ikkrasfvnlsafdtslfqralallessmylnshqlyqkvaqeilvsqilpnlqqsdelqtyflavlnalfikapderrqemanflaoka
Mouse ELMO1  181
Rat ELMO1    181
CHO-ELMO1    181

Human ELMO1  271  lrsllltfvfraqralmesmahglyvlqvlfnlsdrmatkdpqdqerdlfelrlaldaesepnsqsmeknsmycrdykklq
Mouse ELMO1  271
Rat ELMO1    271
CHO-ELMO1    271

FIG. 13A

```
Human ELMO1  361  finhvnpamdftqtppgmlaldnmlyfakhhqdayirivlenssredkhecpfgrssieltkmlceilkvgelpsetcndfhpmffthdr
Mouse ELMO1  361  ..........................................................................................
Rat ELMO1    361  ..........................................................................................
CHO-ELMO1    361  ..........................................................................................

Human ELMO1  451  sfeeffciciqllnktwkemratsedfnkvmqvvkeqvmralttkpssldqfkskIqnlsyteilkirqsermngedfqsrpilelkeki
Mouse ELMO1  451  ..........................................................................................
Rat ELMO1    451  ..........................................................................................
CHO-ELMO1    451  ..........................................................................................

Human ELMO1  541  qpeilelikqqrlnrlvegtcfrklnarrrqdkfwycrlspnhkvlhygdleespqgevphdslqdklpvadikavvtgkdcphmkekga
Mouse ELMO1  541  ..........................................................................................
Rat ELMO1    541  ..........................................................................................
CHO-ELMO1    541  ..........................................................................................

Human ELMO1  631  lkqnkevlelafsilydsncqlnfiapdkheyciwtdglnallgkdmmsdltrndldtllsmeiklrlldleniqipdapppipkepsny
Mouse ELMO1  631  ..........................................................................................
Rat ELMO1    631  ..........................................................................................
CHO-ELMO1    631  ..........................................................................................

Human ELMO1  721  dfvydcn
Mouse ELMO1  721  .......
Rat ELMO1    721  .......
CHO-ELMO1    721  .......
```

RANDOM HOMOZYGOUS GENE PERTURBATION TO ENHANCE ANTIBODY PRODUCTION

CROSS REFERENCE TO RELATED CASES

This application is a continuation of application Ser. No. 11/928,393, filed Oct. 30, 2007, now U.S. Pat. No. 7,745,148 allowed, which claims the benefit under 35 U.S.C. §119(e) of U.S. Provisional Patent Application No. 60/855,127, filed on Oct. 30, 2006, which is incorporated by reference herein in its entirety.

STATEMENT REGARDING FEDERALLY SPONSORED RESEARCH

This invention was made, in part, with U.S. government support under Defense Advanced Research Project Agency (DARPA) Agreement No. W91NF-050C0059. The United States Government may enjoy certain rights pursuant thereto.

BACKGROUND

1. Technical Field

The present invention relates to methods of altering cells to enhance production of proteins they have been raised to express. Particularly, this invention addresses the use of Random Homozygous Gene Perturbation to enhance antibody expression of an antibody-expressing host, by targeted insertion of DNA to either depress endogenous expression of a host protein, or enhance expression of a poorly expressed host protein, the change in expression being related to an increase in expression of the antibody expressed by the host cell.

2. Background of the Technology

Antibodies, particularly monoclonal antibodies, have become important biologic products both in mankind's arsenal against disease, and in research and development. While not the "magic bullet" once envisioned, more than a score of monoclonal antibodies, sometimes referred to as mAb, have been approved for therapeutic use. Just a few of these include the Trastuzumab antibody, the active agent in Herceptin® approved for the treatment of some breast cancers, Palivizumab, the mAb of Synagis® approved for the prevention/treatment of RSV, and Bevacizumab, a mAb present in Avastin®, approved for the treatment of colorectal cancer, and indicated to be effective in treating other conditions. Many more are known.

By contrast, there are literally thousands of antibodies, mAb and polyclonal, employed as workhorses in laboratories and research facilities around the world. Antibodies are useful as diagnostics, as agents to bind and isolate target molecules, to differentiate cells for testing, and other uses that take advantage of the specific binding properties of IgG to select out a single antigen, typically a biological molecule, bound or unbound, that may be of interest. Antibody production is fundamental business.

Methods of making antibodies are well established, although refinements are added constantly. The basic information was set forth as early as 1975, Kohler & Milstein, Nature, 256: 495-497 (1975). To prepare monoclonal antibodies, a host, typically a rabbit or the like, is injected with the antigen against which a mAb is sought. Following immunization, the spleen, and possibly lymph nodes, of the host are removed and separated into single cells. These cells are then exposed to the target antigen. Cells that express the desired mAb on their surface will bind to the immobilized antigen. These cells are cultured and grown, and fused with myeloma cells or other immortal cells to form hybridoma, which can be cultured to recover the expressed antibody.

Most antibodies, and virtually all therapeutic antibodies, need to be modified to avoid inducing a rejection reaction in a patient. The DNA encoding the antibody expressed by the hybridoma is isolated, and can be modified by the insertion or removal of bases, altered glycosylation profiles, and manipulation of framework regions and complementary determining regions, which affect the affinity and avidity with which the antibody binds to its target antigen. The resulting antibodies are humanized or "human" or otherwise modified (chimeric antibodies and veneered antibodies are common in the art). The state of the art as of about 1995 is reflected in U.S. Pat. No. 6,054,561, the relevant disclosure of which is incorporated herein by reference.

Once prepared and isolated, the DNA encoding the antibody may be transferred to a preferred mammalian cell line for expression in "production" or commercial amounts. It has long been recognized that Chinese Hamster Ovary cells (CHO cells) make excellent expression vehicles for recombinant or non-endogenous DNA. See U.S. Pat. No. 4,816,567. There has been developed a series of DHFR deficient CHO cell strains, which permit the amplification of inserted DNA encoding specific proteins or DNA sequences, as set forth in U.S. Pat. No. 5,981,214. This latter patent describes the use of homologous recombination to target a specific gene or expression region of a cell—in the case in question, to induce expression of a heterologous gene. Other suitable cell lines include 293HEK cells, HeLa cells, COS cells, NIH3T3 cells, Jurkat Cells., NSØ cells and HUVEC cells. Other mammalian cell lines suitable for the expression of recombinant proteins have been identified in the literature, and are equally suitable for use in the invention of this application.

Once stabilized, current methods to increase production of the valuable antibodies tend to focus on increases the total productivity, that is, high volumetric productivity, so that a given amount of cells produces a given amount of antibodies. These methods tend to focus on improving the methods and environments used to cultivate the cells, to enhance total antibody production. In general, antibody production of greater than about 1 g/L is required for an industrially competitive process. Individual CHO cells are typically expressing in the range of 10-15 pg/cell/day.

Homologous recombination has been used in many contexts since about 1985. It was originally employed as a "knock-out" tool, allowing the suppression of an expressed gene, to study the response of the modified cell. Subsequent procedures were developed to allow the silencing of target genes. The use of anti-sense knock out constructs using a random homozygous knock out method (RHKO) is described, e.g., in Li et al, Cell 85: 319-329 (196). In U.S. Patent Publication 20060240021 (U.S. patent application Ser. No. 10/524,426 filed Aug. 18, 2003) the use of RHKO techniques is disclosed to identify the genes involved in rapamycin resistance. The entirety of that disclosure is incorporated herein by reference. The ability to insert a construct into one allele, identify the cells where that allele has been successfully modified by quick throughput searching, such as for example by FACS (fluorescence activated cell sorter) and similar methods makes this a superior technique for selective identification and modification of a cell's genome. U.S. Pat. No. 6,835,816, incorporated by reference herein discloses the use of this technique in conjunction with genes reflecting tumor susceptibility, including TSG101 genes.

Accordingly, it remains a goal of the industry to find a way to increase the expression of antibodies, particularly recombinantly prepared antibodies, from expression hosts like CHO cells, 293HEK cells, HeLa cells, COS cells, NIH3T3 cells, Jurkat Cells, NSØ cells and HUVEC cells. and others, in a stable and reproducible fashion, using available techniques to modify the genome of the cell.

SUMMARY

The invention demonstrates that cells that are good expression vehicles for recombinant antibodies can be modified to increase the specific productivity rate (SPR) of antibody producing cells by a factor of 1.5, 2 or even 3 fold above the expression range capable of the cell without such modification. Thus, by selectively altering the expression profile of the cell, using knock out techniques (Random Homozygous Gene Perturbation or RHGP) or expression enhancement techniques by inserting expression promoters rather than anti-sense RNA or other expression suppression constructs, antibody production by the cell can be enhanced. Enhancement values of 3-fold or more, SPR, have been achieved by suppression of the expression of targeted proteins. Enhanced SPR leads to enhanced volume productivity, permitting commercial collection of mAb on a heretofore desired but not achieved basis.

BRIEF DESCRIPTION OF THE DRAWINGS

FIG. 3 is an illustration of the assays that can be used to demonstrate enhanced antibody expression by cells transformed according to the invention.

FIG. 13 reflects the sequence for the Elmo1 gene of humans, mice, rats and as present in CHO cells transformed by the invention.

DETAILED DESCRIPTION

Figure 1:
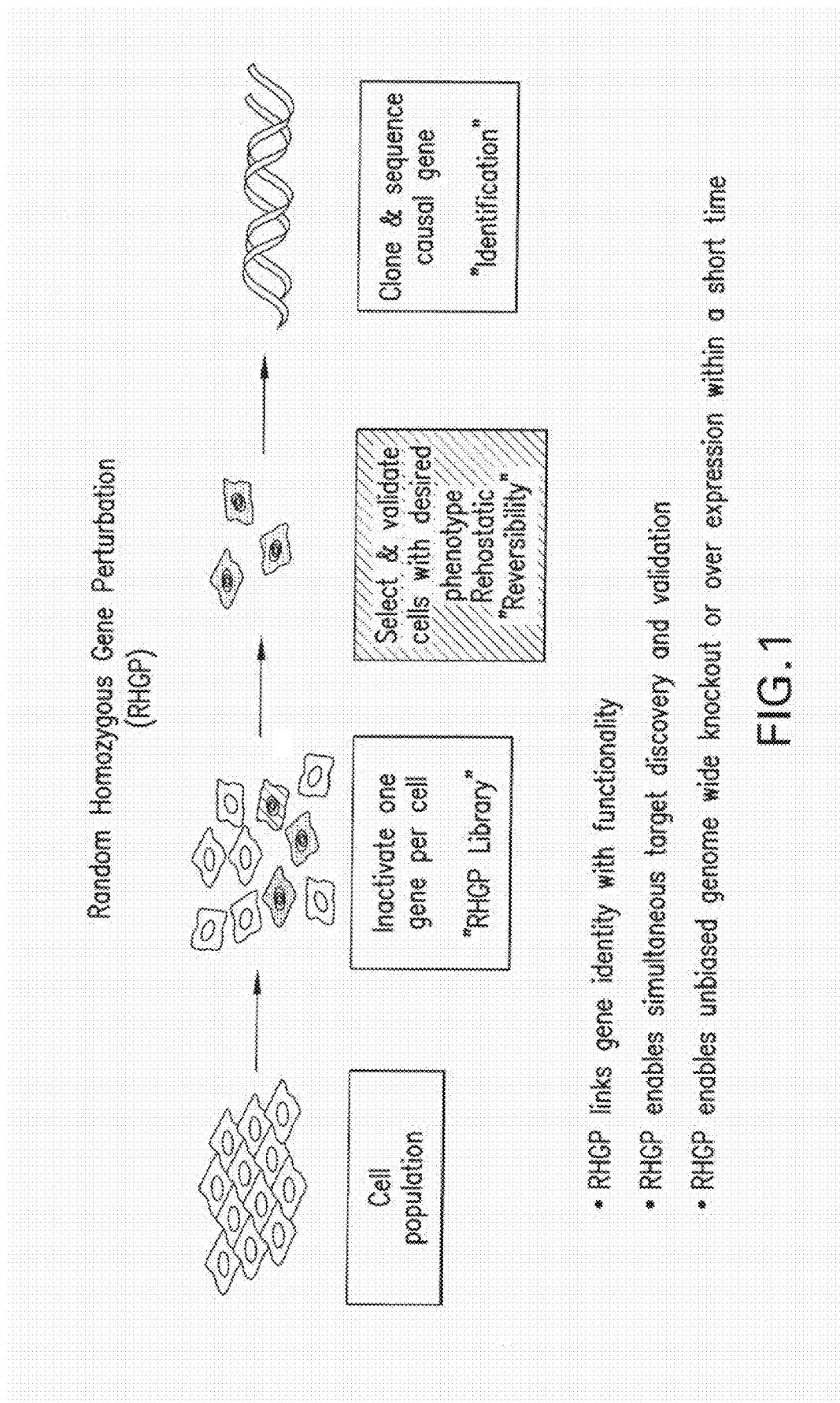
FIG. 1 is a schematic illustration of the process of the invention.

Applicants' invention resides in the discovery that the Specific Productivity Rate or value of anti-body producing cells can be enhanced by altering the expression profile of the cell's endogenous genome without altering the genomic sequence about the antibody itself. Thus, as noted above, it is possible to insert expression enhancers, amplifiable genes, and the like, proximate to, or with, the inserted heterologous DNA that expresses the mAb of interest. These methods have their limits. Applicant's invention lies in the discovery that by inserting a construct at a locus other than that which encodes the antibody itself, protein expression profiles may be altered, thereby increasing he SPR for the antibody. In many cases, this will involve introducing a knock-out construct . . . and insert encoding, for example, anti-sense RNA, to down regulate or suppress expression and even translation of a particular protein. In other situations, it will involve inserting an expression construct, or a construct involving an enhancer or promoter or some other activator that enhances expression of a non-mAb protein, which is implicated in the mAb synthesis pathway, and thus upregulates mAb expression.

This is conveniently affected, in one example, by insertion of an anti-sense knock-out construct that deactivates or inactivates an unrelated protein. Not all knock-out or down regulation will increase mAb expression. There does not appear to be at this time a way to map the proteins whose expression profile can be affected in a way to predict whether that alteration will increase SPR of a given cell. Predictably, there are some proteins whose expression cannot be significantly downregulated without adversely affecting survival of the cell. By the same token, it is quite possible to increase expression of certain proteins to the point where they are toxic to the cell. Applicants' invention lies between these two extremes.

In general, there are two ways to improve antibody yield, theoretically. One is to increase total productivity of a given quantity of antibodies. There are limits on the improvements that can be made without affecting the individual antibody-expressing cells. While one can improve culture/fermentation conditions, improve spacing and the like, real world limitations on the cost and capability of processing hardware, the costs and frequency of media replacements, and the like combine to limit the improvements available by manipulating the environment in which the cells are grown to fractional or incremental improvements.

An alternative approach is to change the expression characteristics of the cells themselves. If substantial improvements in cell SPR can be made, without huge losses in volumetric productivity, and overall increase in antibody yield is obtained. Applicants have discovered that in fact SPR can be increased, as much as 300% or better, without a concomitant loss in productivity of a given volume of cells, giving an overall increase in antibody expression. Enhanced Antibody Production (EAP) is thus achieved by insertion of a DNA construct at a locus distant from the locus of the inserted antibody encoding sequence. This makes it possible to increase the level of expression without endangering the characteristics of the antibody itself or the insert region, which may be critical to the expression of the heterologous antibody. Quality control is satisfied by ensuring that the mAb products of cells exhibiting EAP bind with the same relative avidity and affinity to the same target as cells of the parent strain, before enhancement.

Figure 2:
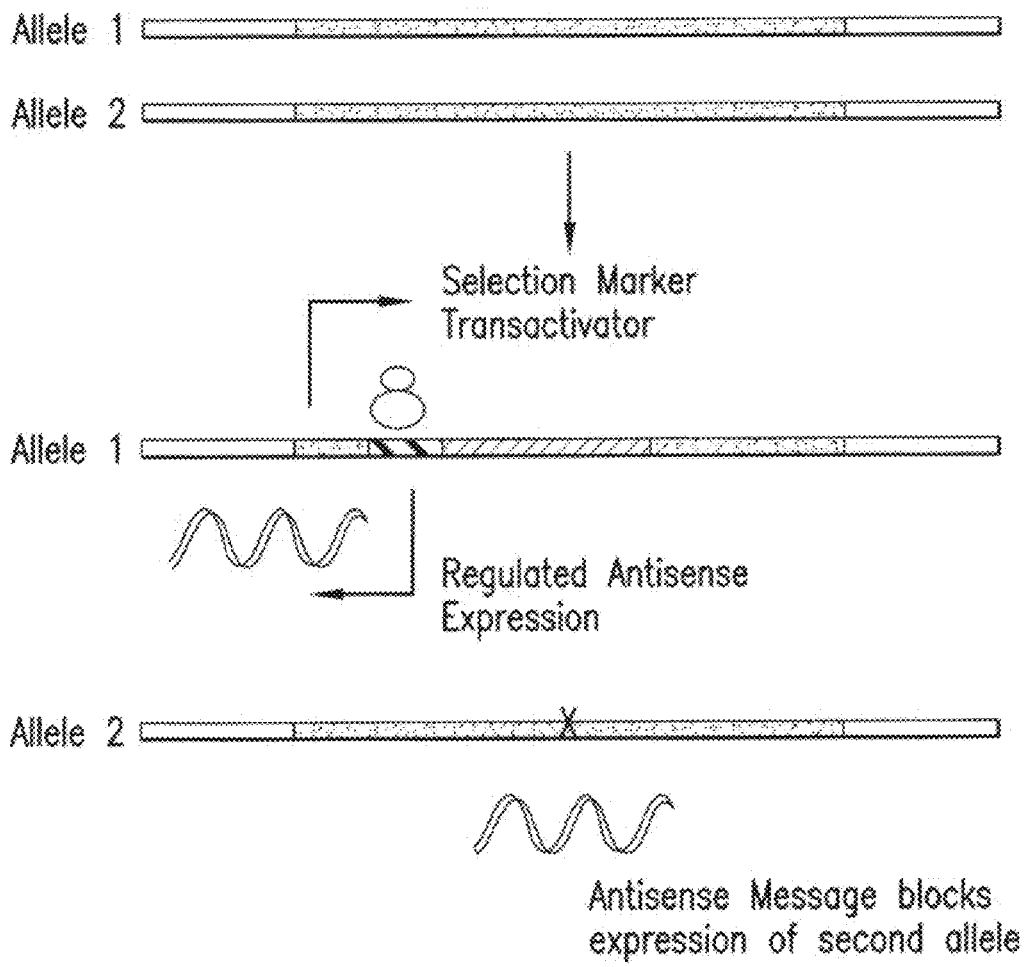
FIG. 2 is a schematic illustration of the modification of a cell line genome by random homozygous gene perturbation according to the invention.

The process is generally indicated in FIG. 1, which constitutes a kind of flow chart for the process of the invention. RGHP is used to inactivate one gene per cell in a population of cells, thus creating a RHGP library. The constituent cells of the library are subjected to a high throughput assay system for the detection of enhanced IgG production. The cells are altered using a Gene Search Vector (GSV) as illustrated in FIG. 2. When integrated into an allele of the target cell, the inserted construct is expressed—generating, in the embodiment illustrated, an anti-sense RNA which effectively reduces expression of the target protein. In alternative embodiments, the GSV may comprise a sequence or fragment which boosts expression of the target protein.

The constituent members of the transformed library are then subjected to a high throughput screening process, to identify candidates exhibiting EAP. One assay in particular that lends itself to this process is FACS. This is because transformed ells that express more antibody on their surface will secrete or release more antibodies. Thus, a rapid and high throughput low cost screening process selects out promising candidates whose mAb expression level are higher due to transformation by the GSV. To confirm that the high producers are in fact expressing the antibody of interest, the pool selected is subjected to a conventional ELISA assay, ensuring the antibodies secreted by the selected cells do in fact bind to the target antigen.

Figure 4:
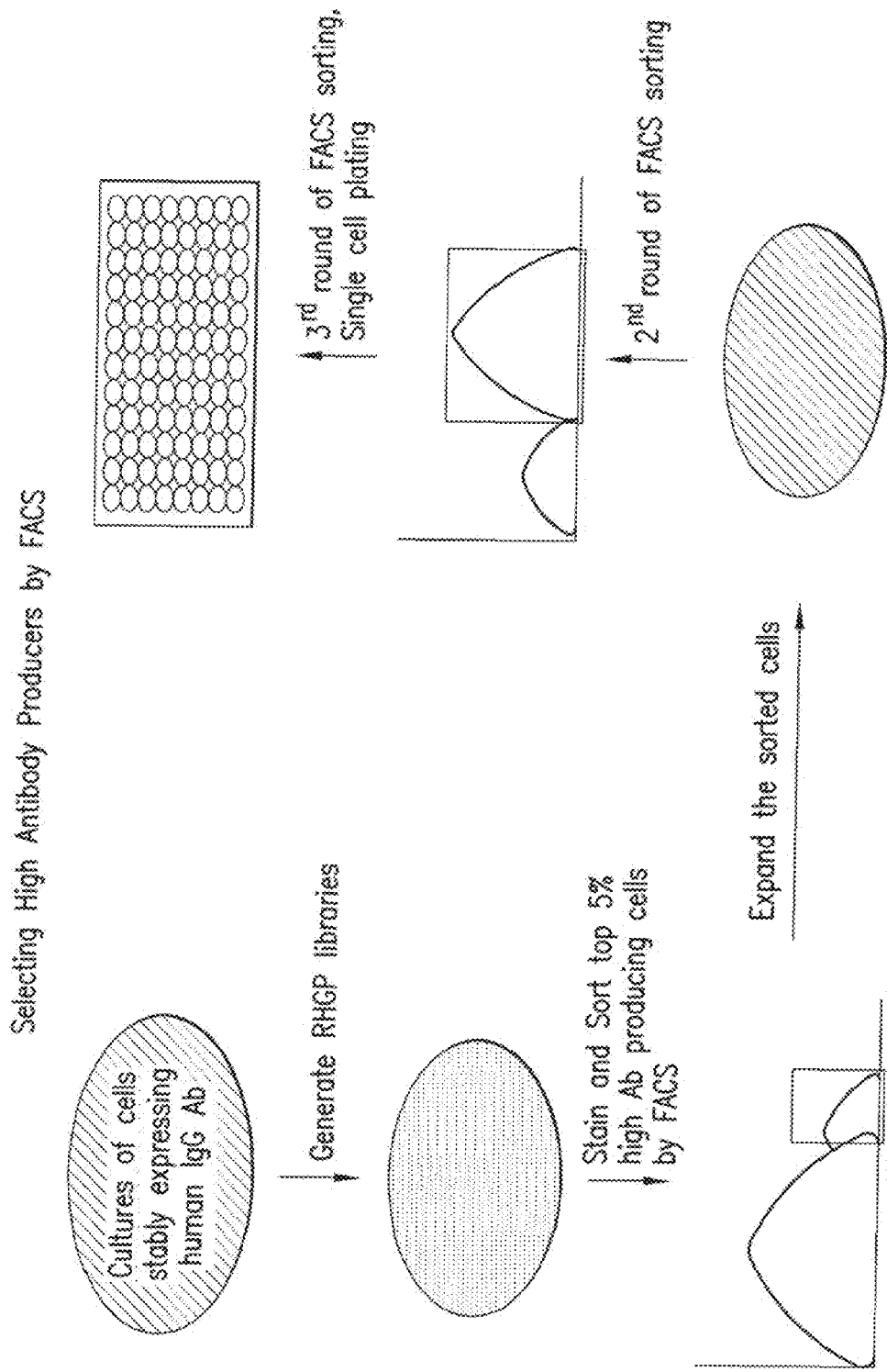
FIG. 4 is an illustration of how the repeated use of FACS sorting assays can enable sequestration of the cells exhibiting the highest SPR for a given antibody through the invention.

It will be appreciated that many cells will respond to the initial transformation by giving some gains in mAb SPR. To achieve the goals of this invention, that is enhancing SPR by as much as 1.5 fold, all the way up to 3-fold and beyond, only the most responsive transformants will be selected. FACS screening, as described above, permits rapid identification of EAP cells, in large amounts. This process is illustrated in FIG. 4, where a first selection of, e.g., the top 5% (the percentage collected will vary with the cell population, and it may be anything from 25% down to 5%—representative values being between those two endpoints, including 10, 15 and 20 percent by way of exemplification). This "first cut is expanded, and subjected to a second round of FACS sorting, again selecting a small percentage of the antibody-expressing cells showing the highest SPR. This second collection is then subjected to a third round, through single cell plating and culturing conditions—yielding stable populations of antibody-expressing cells exhibiting EAP and significantly higher SPRs than the original parent strain prior to manipulation through RHGP.

Figure 5:
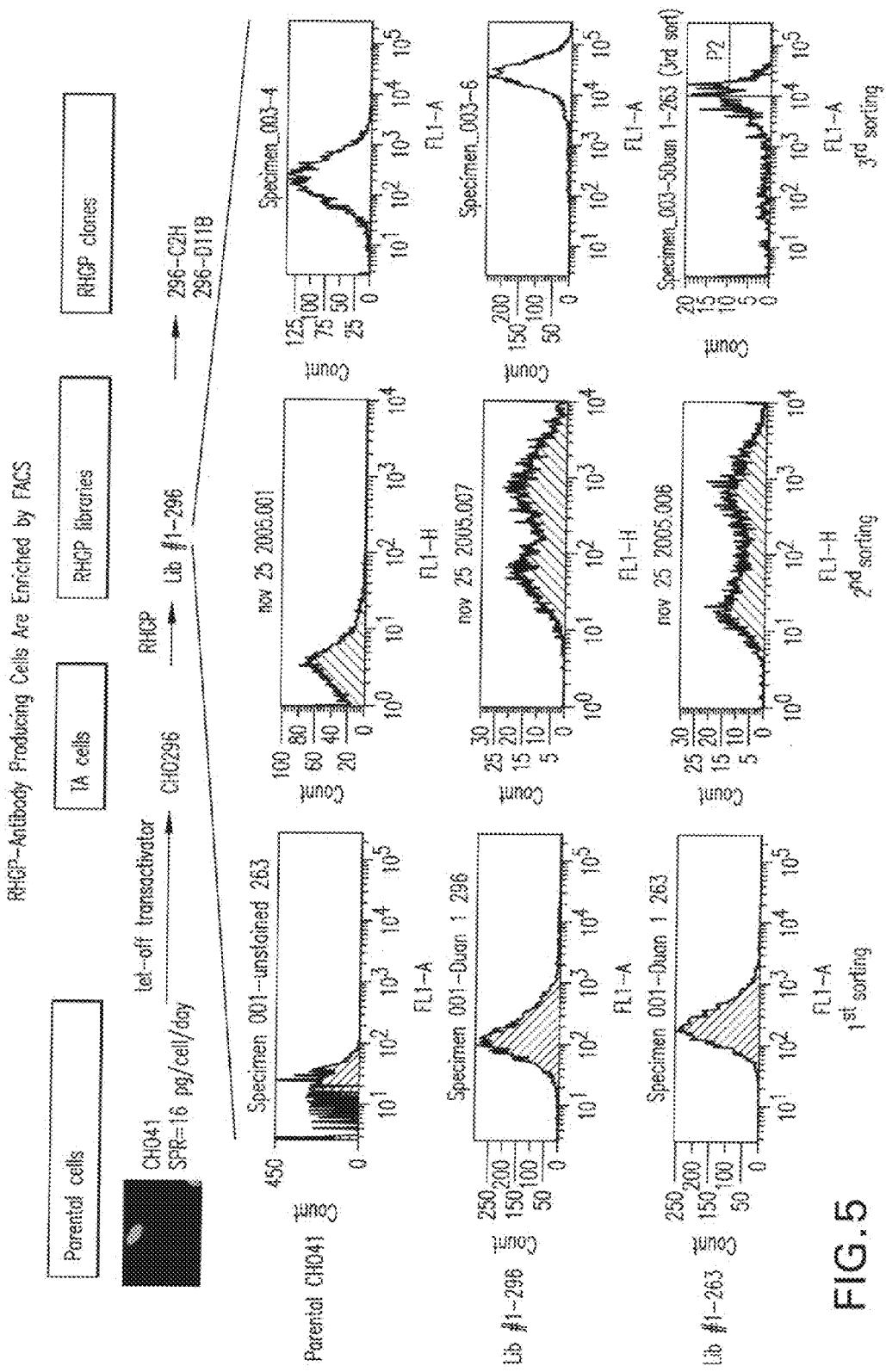
FIG. 5 is a schematic demonstrating the SPR enrichment for cell lines transformed according to the invention using repeated FACS assays.

As shown by actual example discussed, infra, involving decreased expression of the Elmo1 gene, in fact, FACS can be used as described above, to enhance antibody-production values, and SPRs, of RHGP transformed cells. The repeated FACS selection "right-shifts" the population of antibodies, with each sorting giving rise to a population with a higher SPR—whether measured by mean, median or mode. The actual utility of FACS sorting according to the invention is illustrated in FIG. 5.

Total volume productivity (TVP) screens are faster and easier to do than selecting out individual improvements in SPR. Thus, the process can be accelerated by taking a total productivity measure for all the members of a transformed library. Since total productivity correlates with SPR, by selecting out high productivity lines, likely sources of high mAb expressing cell lines are the highest volume productivity cell lines. Thus, FIG. 6 reflects an extinction experiment in which volume productivity for an entire library of potential transformants is measured, following RHGP. Thus, a number of cell lines actually show inferior volume productivity, while the majority show at least some degree of improvement, when compared with the non-transformed rent line.

Figure 6:
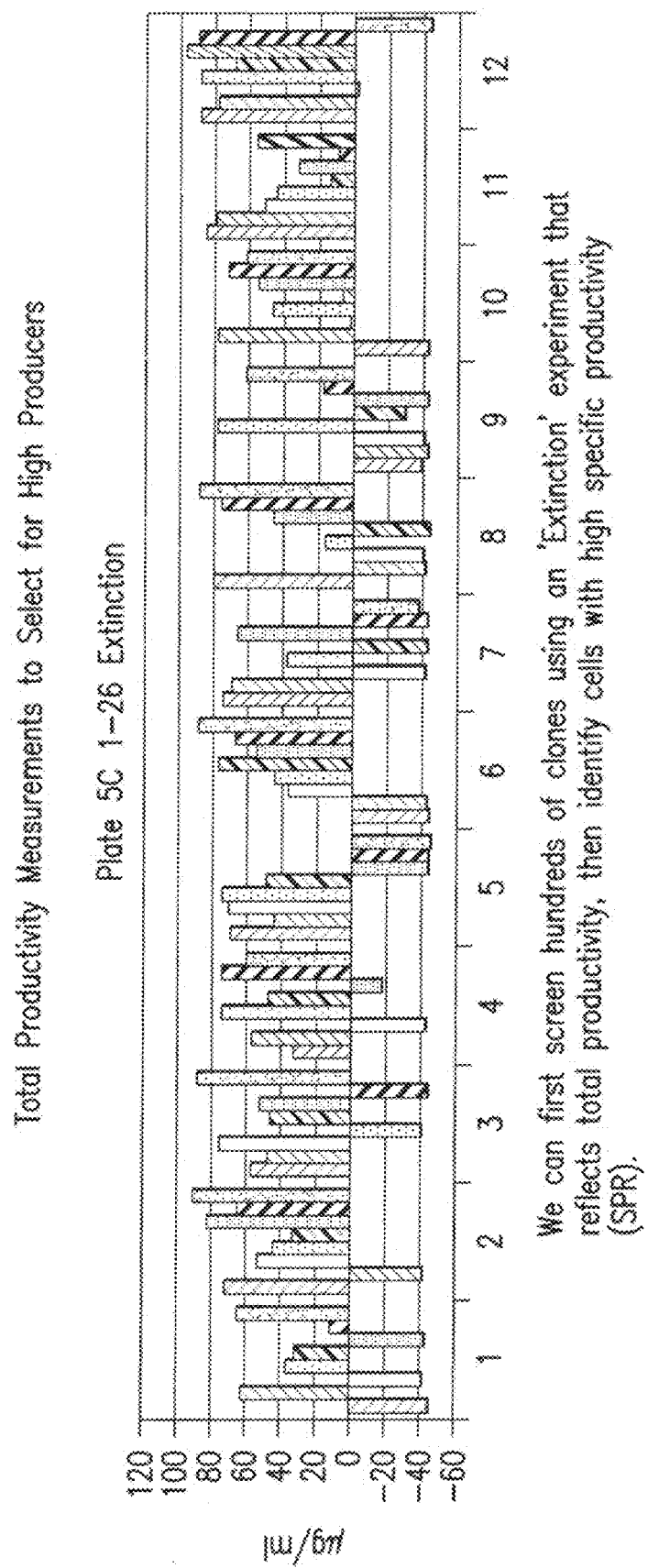
FIG. 6 is a graph showing the distribution of SPR for cells modified by RHGP as compared with parent expression values.
Figure 7:
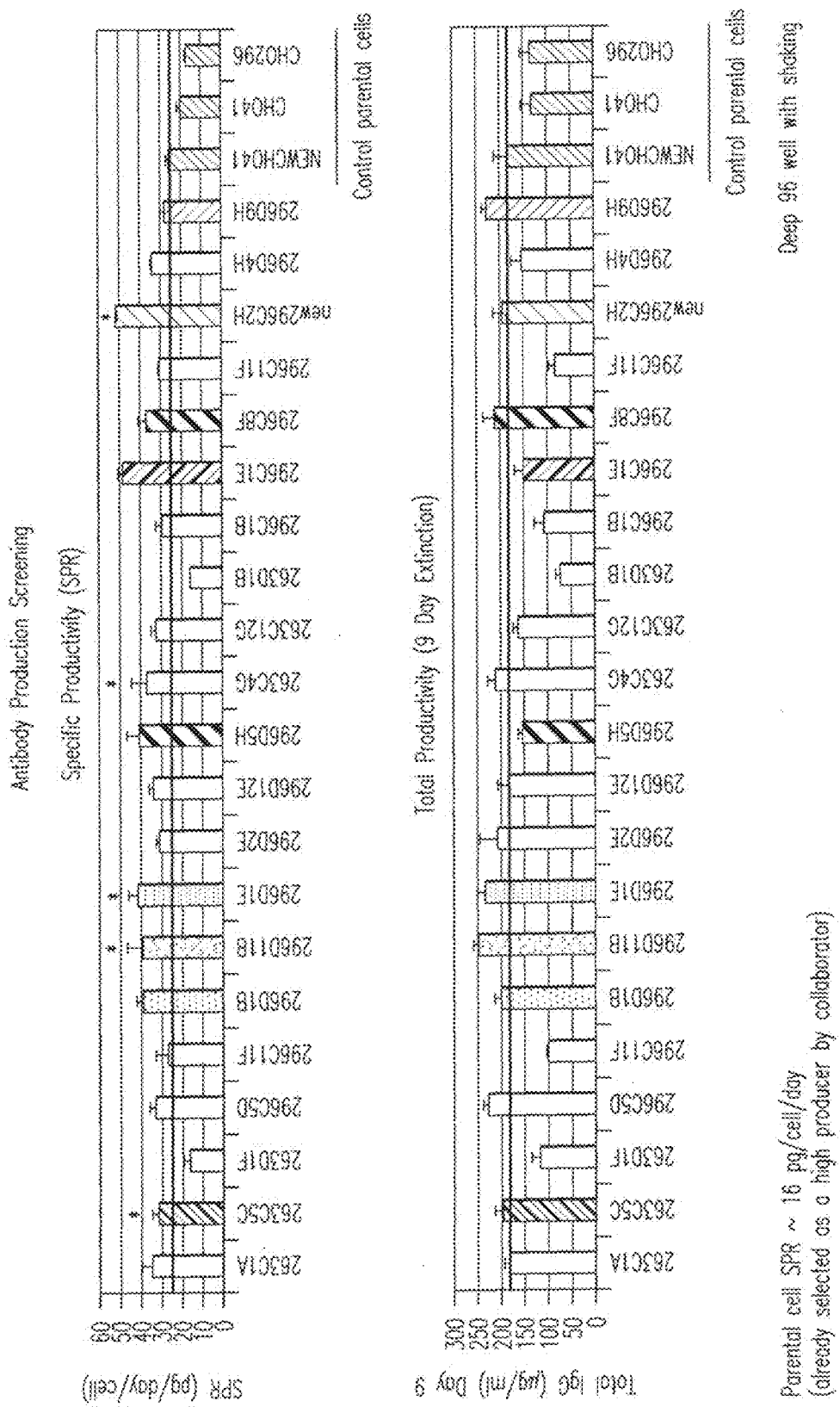
FIG. 7 is a graph comparing SPR and TPV for cells exhibiting enhanced SPR values following RHGP t reduce Elmo1 expression levels.
Figure 8:
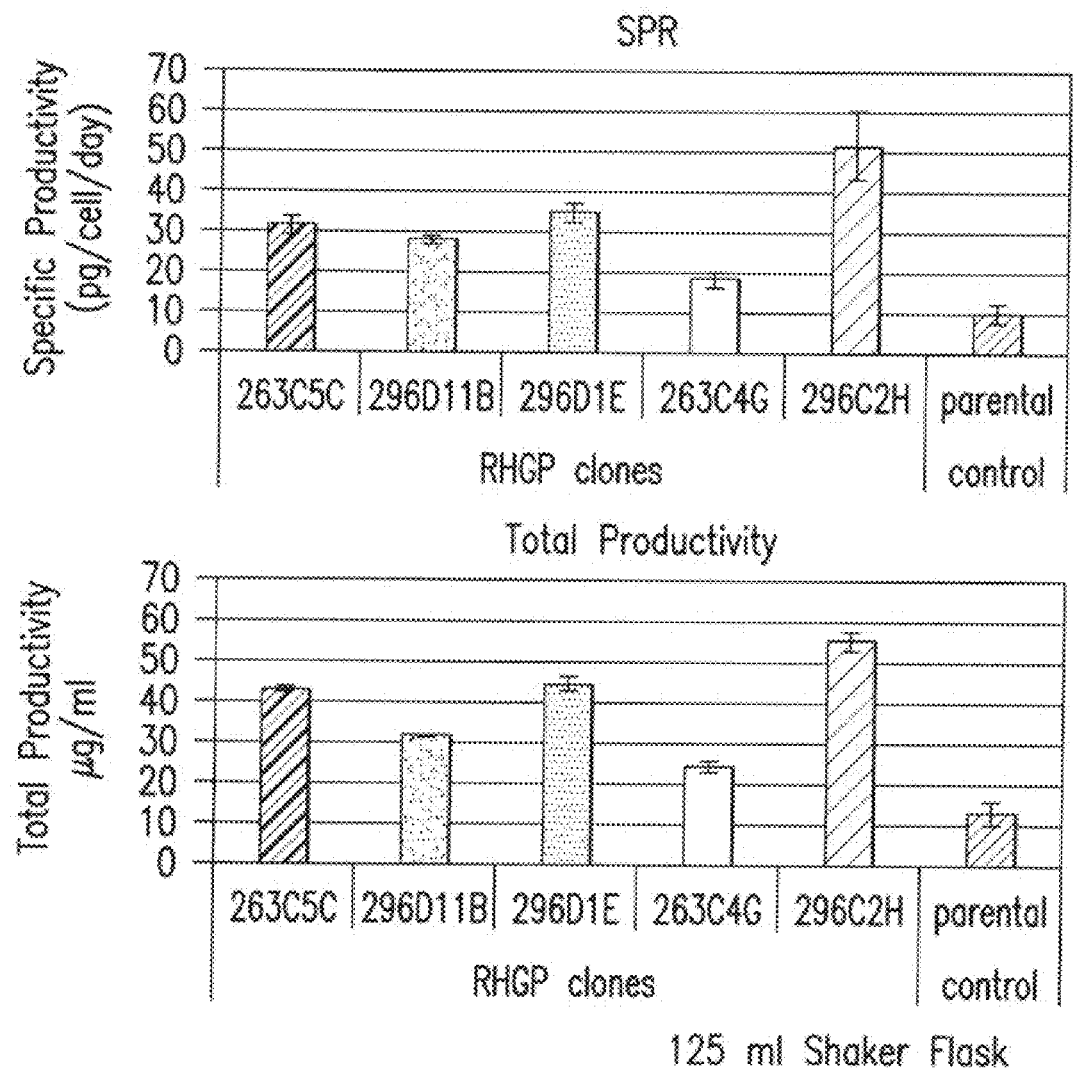
FIG. 8 is a graph showing 3-fold enhancement of SPR and TPV using the process of the invention.
Figure 9:
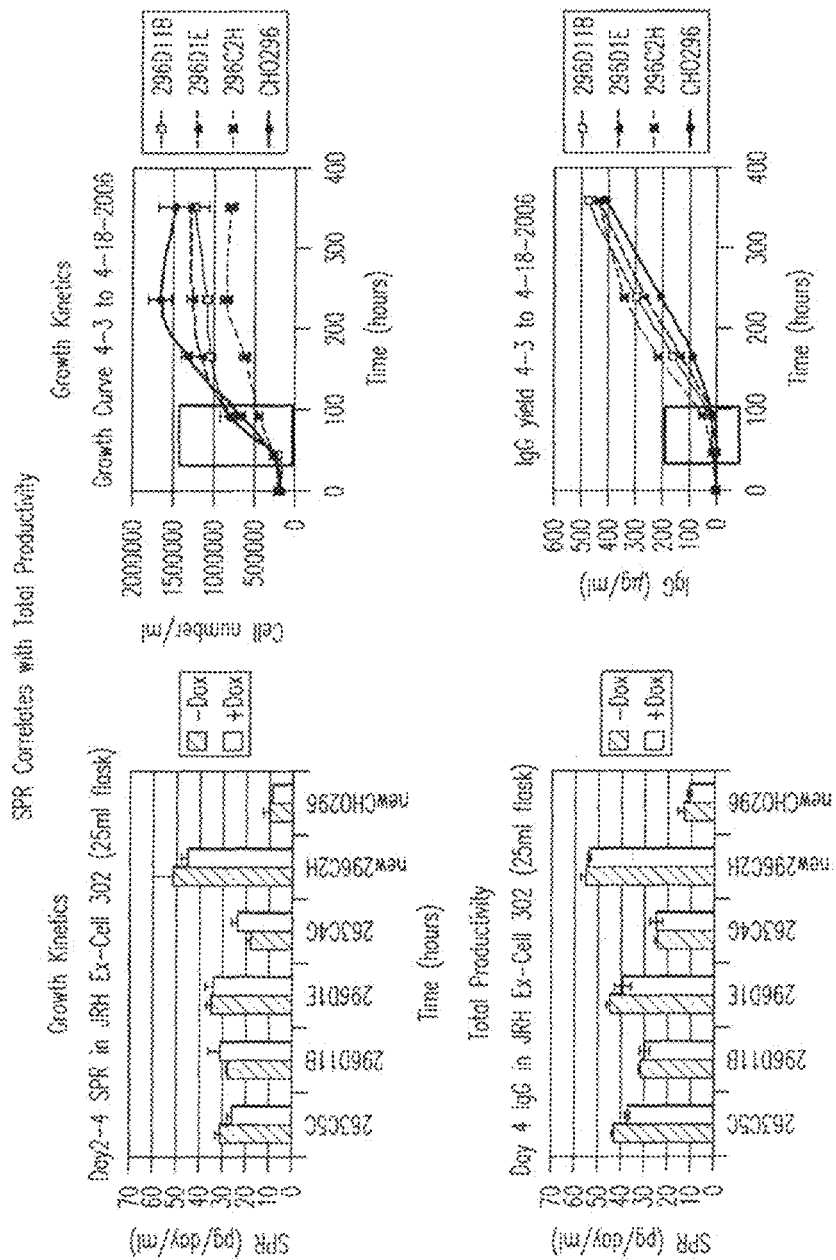
FIG. 9 is a four part graph demonstrating correlation of SPR with TVP of cells transformed with RHGP according to the invention.

The cell lines giving the highest volume productivity values from the experiment reflected in FIG. 6 (this was done with the Elmo1 experiment set forth below—giving actual experimental values) were measured for SPR as shown in FIG. 7, All but two of the cell lines giving a higher total productivity on a 9-day extinction experiment gave SPR values better than the parents—and as show, the parents were selected for an already high SPR of 16 pg/cell/day. Cell lines expressing >50 pg/cell/day may be secured through this invention. This is illustrated in FIG. 8, where at least one cell line, 296C2H, prepared by RHGP insertion of the Elmo1 anti-sense RNA exhibited both SPR and volume productivity in excess f this target value. All of the selected cell lines illustrated show marked improvements in their SPR when compared to the high-producing parent. Thus, given a simple transformation step well away from the cite of the transforming antibody sequences, significant increases in antibody expression are achieved. The correlation between SPR and total productivity is also shown in FIG. 9, which shows growth kinetics for the various cell lines. Depending on the envisaged facility and industrial or commercial process, growth kinetics may impact the choice of the "best" modified cell to select, given relatively similar TVP and SPR.

Figure 10:
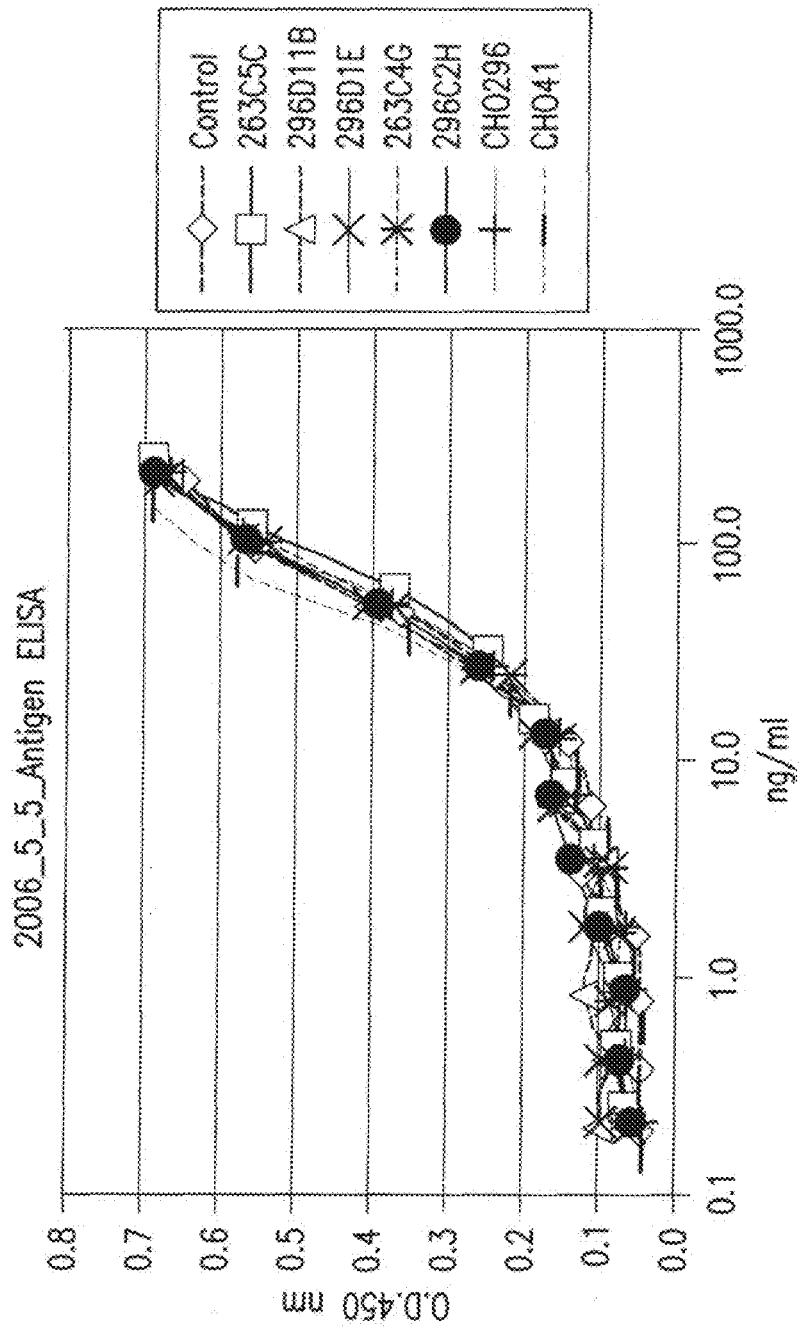
FIG. 10 is a graph demonstrating the similarity in binding properties of antibodies expressed by cells transformed by RHGP to exhibit higher SPR values with parent cells of same cell line that did not undergo RHGP.
Figure 11:
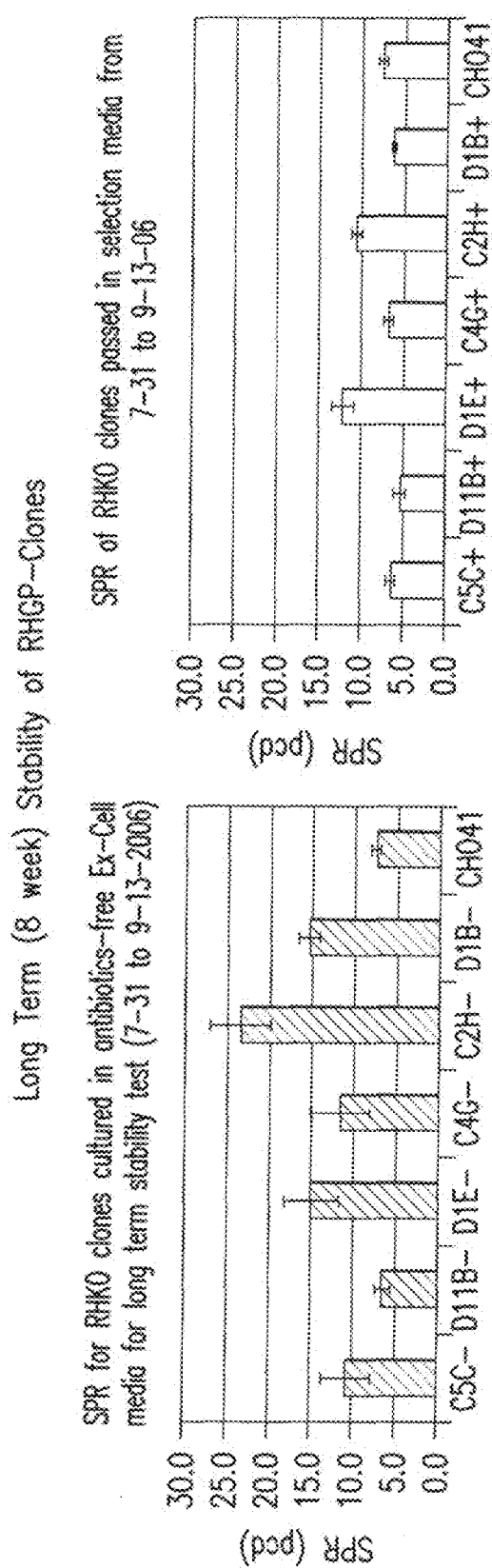
FIG. 11 is a graph demonstrating long term stability of CHO cell clones modified by RHGP to enhance antibody SPR.
Figure 12:
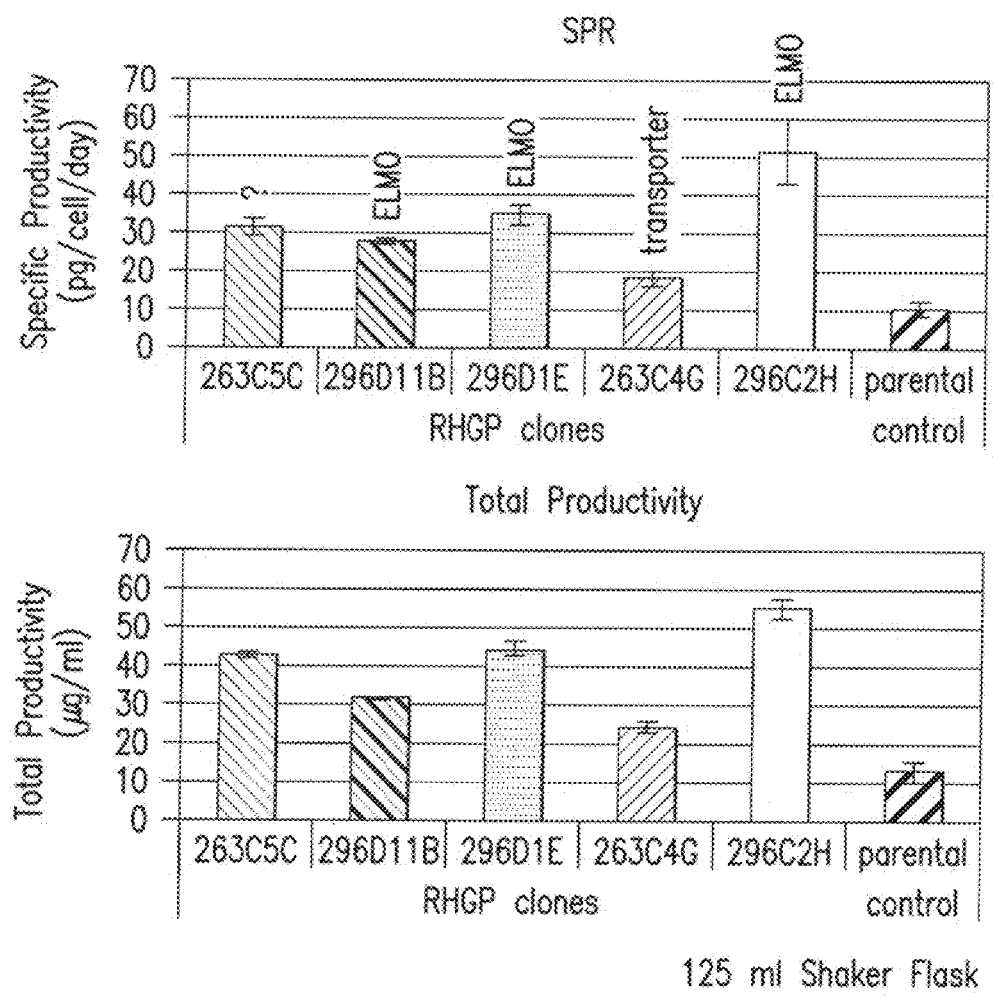
FIG. 12 is a graph demonstrating the presence of elevated SPR and TVP by several clones of a CHO cell line obtained by RHGP-induced downregulation of Elmo1 expression.

As noted above, it is important to develop a technique that is not only simple, susceptible of application on a rapid throughput format, and capable of giving substantial improvements in the SPR of a given mAb-producing cell line, it is essential that the transformation take place in a site remote from the antibody sequences themselves, so that antibody properties are not disturbed. As shown in FIG. 10, the antibodies of the RHGP transformed high SPR cells exhibit binding characteristics not distinguishable from those of the parent strain. In FIG. 10, the parent strain is given as the control. These increases are stable over time. See FIG. 11. Equally important is the transformation induced by RHGP pursuant to the invention results in stable increases in SPR. As shown in FIG. 12, a number of clones from a single experiment involving down regulation of the Elmo1 gene exhibited both higher SPR and higher TVP.

EXAMPLE 1

RHGP Using Antisense RNA of the Elmo1 Gene

The Elmo1 gene of *C. elegans* was identified as important in phagocytosis of apoptotic cells, and for cell migration. Gumienny et al, Cell. 107(1): 27-41 (2001). This gene was targeted with an anti-sense knock-out RHGP, in an effort to improve higher antibody SPR in cells expressing recombinant antibodies. The general strategy described above was employed for this experiment.
Identification of Engulfment Cell Motility 1 Protein Gene Involved in Enhanced Antibody Production.
When the individual phenotypes have been selected for cloning, the target gene involved in enhanced antibody production was identified by the strategy shown in FIG. 1. The vector map for the Elmo1 construct is given in FIG. 14.

The full-length CHO ELMO1 cDNA was cloned into the expression vectors of pCDNA3.1 and pLLexp with both orientations, which allow the over-expression of the ELMO1 protein or production of the antisense RNA. Since the anti- ITP antibody is not available, the CHO ITP cDNA was fused with myc taq at its 5' or 3' end and cloned into pLLexp expression vector. The fusion partner, myc taq will provide a domain for detection for the expressed ITP protein level.

Figure 14:
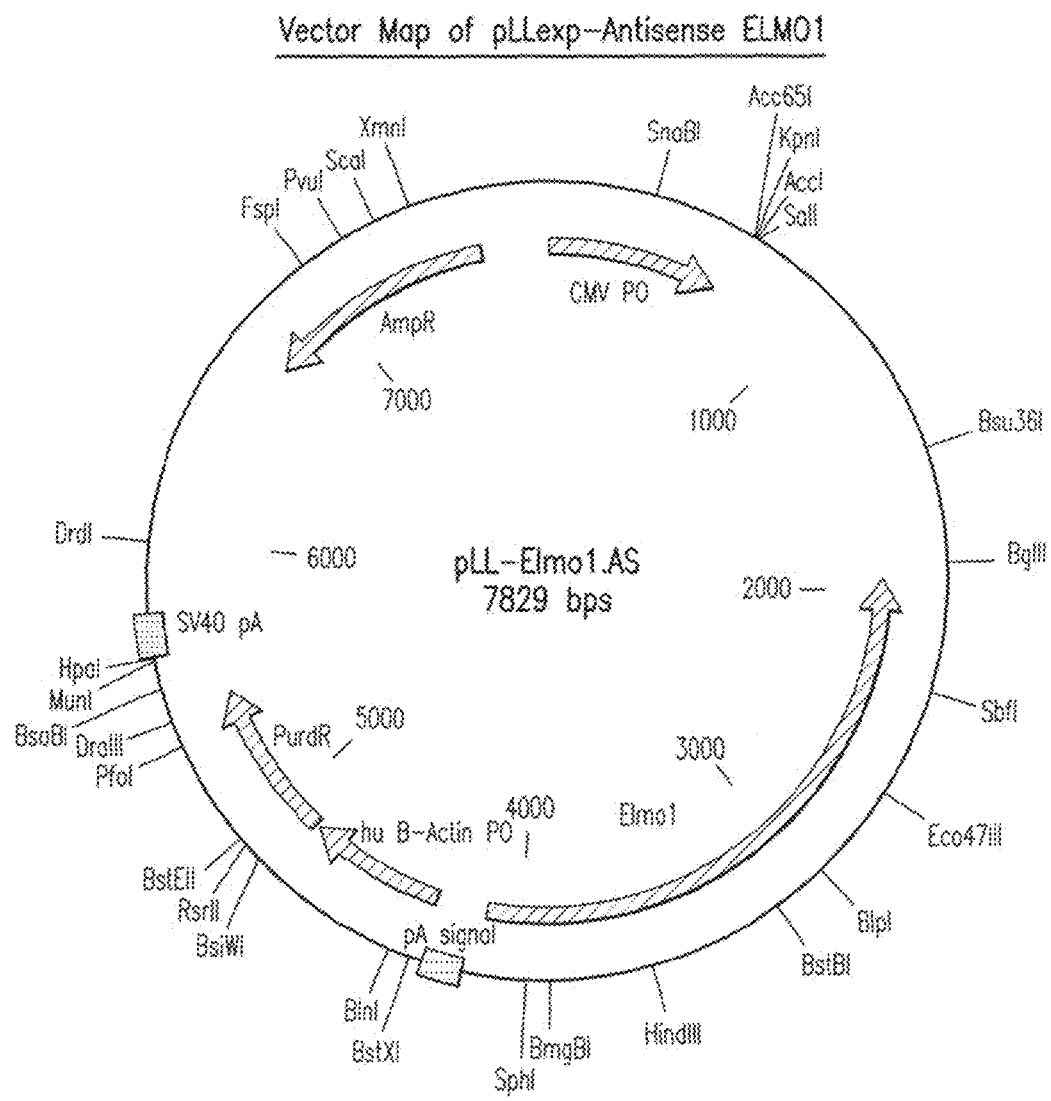
FIG. 14 is a vector map of the plasmid used to induce downregulation of the Elmo1 gene through RHGP according to the invention.

To verify that the phenotypes with higher SPR have the GSV insertion in the genomes, the genomic DNA was first subjected to PCR amplification of the chloramphenicol acetyltransferase (CAT) gene. Indeed, the PCR analysis has indicated that all the single clones and the pools selected by FACS have the CAT gene inserted in the genome. To identify the gene involved in the phenotype of clone 296-C2H, the genomic DNA was digested with restriction enzymes individually, which allow us to rescue the genomic DNA along with the GSV. The digested genomic DNA was re-circulated and used to transform E. coli competent cells. A total of 16-24 transformed colonies were picked for DNA preparation and sequencing analysis with the LTR primers near the junctions between the GSV vector and the genomic DNA. The regenerated genomic sequence was taken for Blast Search in GeneBank. A 450-bp domain of CHO genomic DNA sequence shares 87% identities with the sequence on mouse chromosome 13, in which a gene called engulfment and cell motility 1 protein (ELMO1) was located. Especially, the further sequencing information revealed that the corresponding exon 16 domain of CHO cells shares 95% homology with mouse counterpart. Although the CHO genome sequence database is not available in public databases, it's obvious that the GSV has been integrated in the intron between the exon 15 and 16 in 296-C2H genome and interrupted the ELMO1 gene according to the blast search information. The CMV promoter from the GSV seems to transcribe the antisense RNA and knockdown the ELMO1 gene in the phenotype, which has lead to the antibody production enhancement. The ELMO1 gene has been identified from many other species, such as mouse, rat and human, which has been reported to be involved in the cells motility and required for cell phagocytosis and cells migration. A 3.7-kb full-length ELMO1 cDNA was isolated from a CHO cDNA library using a 31 nucleotide primer designed from exon 16 of CHO ELMO1. The complete coding sequence of ELMO1 from CHO cells is 2181-bp long encoding 727 amino acids protein. The CHO protein shares 99% homology with mouse, rat and human homolog. (FIG. 13). The cDNA was then cloned in pCDNA3.1 and pLLexp expression vector with both orientations for validation of the gene in naive cell line (FIG. 14)

Figure 15:
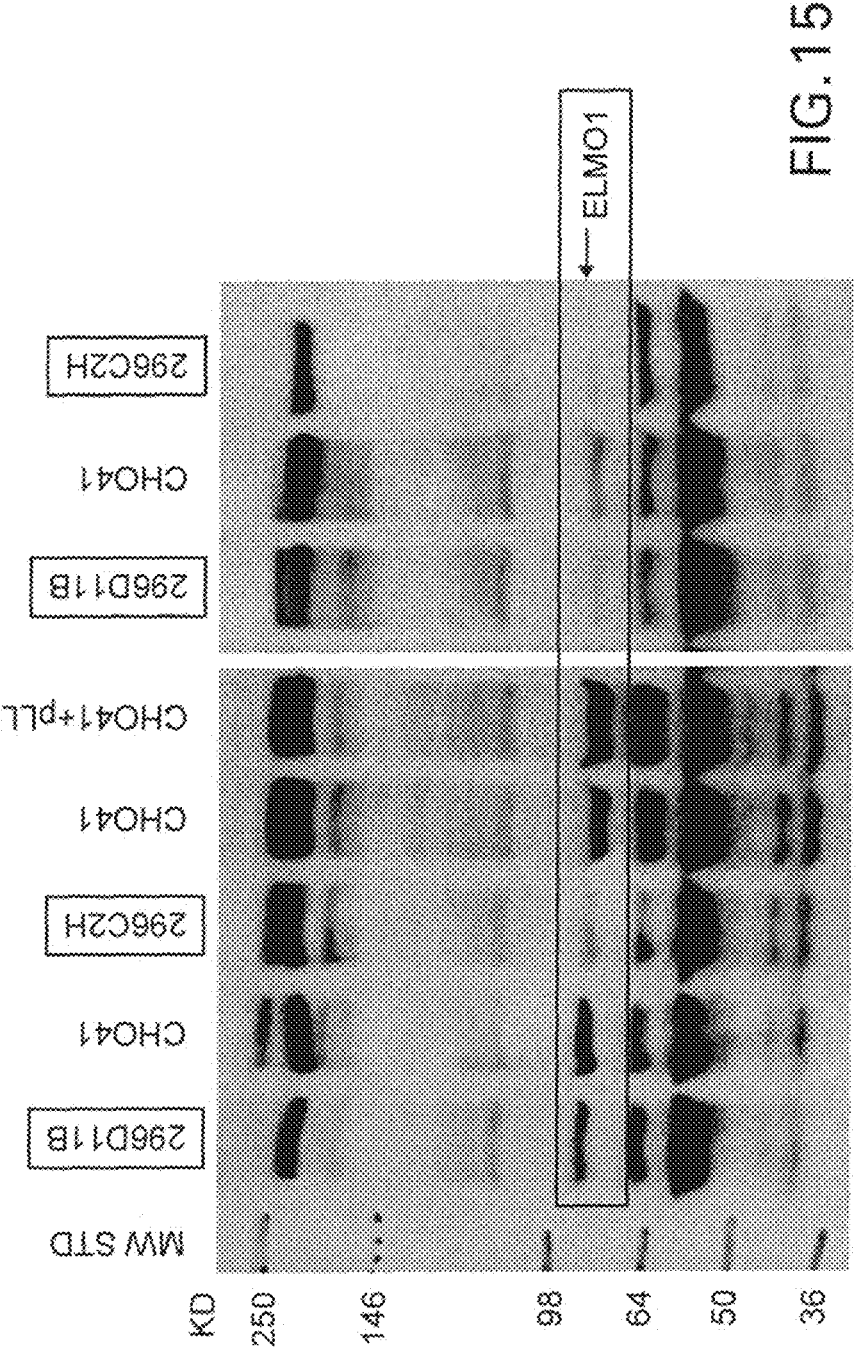
FIG. 15 is a blotting photomicrograph demonstrating downregulation of Elmo1 in cells exhibiting enhance antibody production following transformation by RHGP.
Figure 16:
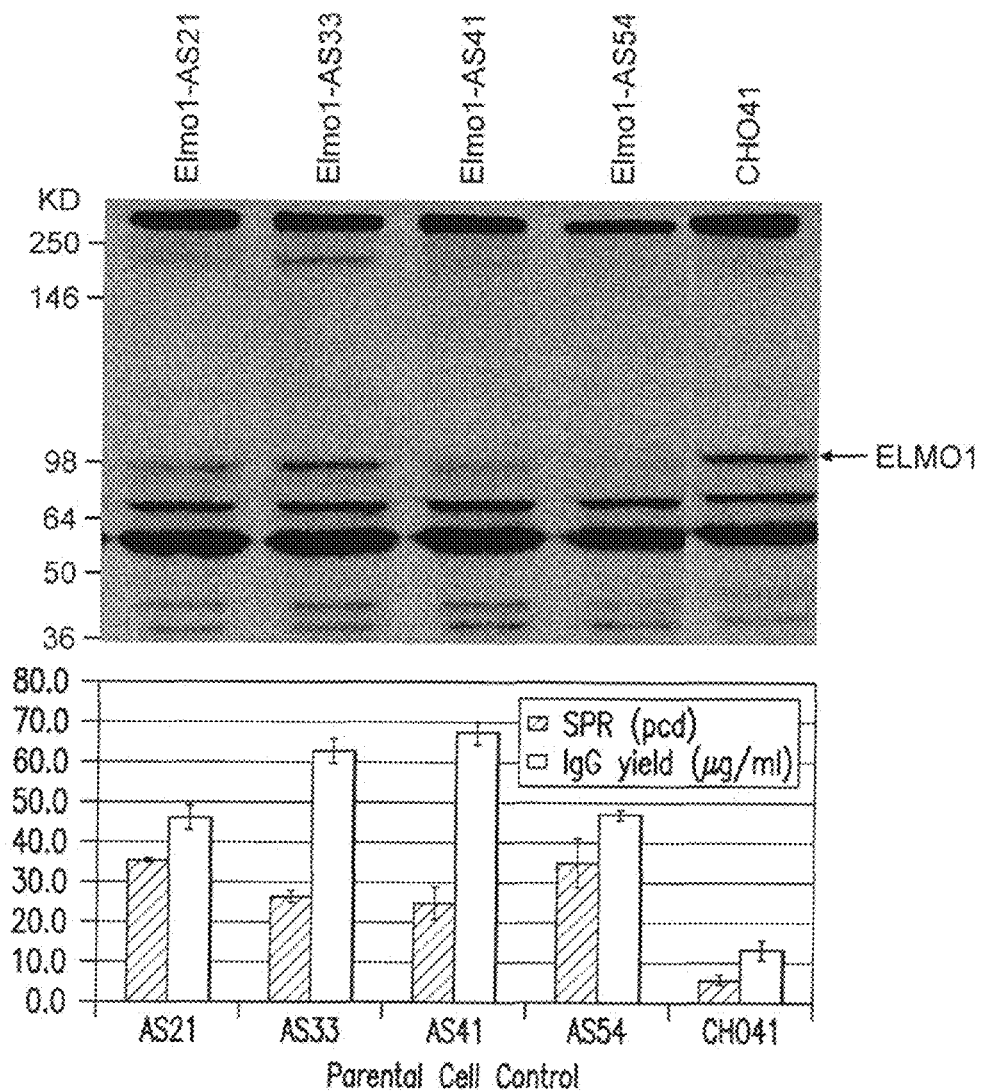
FIG. 16 is a graph demonstrating the increase in SPR of cells modified by RHGP as compared with the decrease in expression of Elmo1.

As discussed above, downregulation of the Elmo1 gene, following insertion of the Elmo1 anti-sense "knockout" construct is correlated with high SPR in RGHP clones from this experiment. See FIG. 15. Importantly however, while some downregulation was observed, it was partial. Elmo-1 is still being produced, as would be expected, given the single allele insertion. In contrast, the increase in SPR and TVP was profound. The two correlated events, induced by a single round of RHGP followed by selection as described above, are shown in a single frame in FIG. 16.

EXAMPLE 2

Ion Transporter Protein

To demonstrate the efficacy of this invention, a second target for RHGP was selected, this time an ion transport protein. What is of fundamental importance is that this experiment demonstrates that proteins can be downregulated (underexpressed as compared with the parent strain expressing the antibody of interest) or upregulated (overexpressed as compared with the unmodified parent strain expressing the antibody of interest) and nonetheless give EAP. What is fundamentally important is that the invention provides a method for modifying the expression pattern of at least one protein of a genome, coupled with a facile method for rapid detection and sequestration of cells expressing antibodies at a significantly higher SPR than the parent cell line prior to transformation by RHGP.

Identification of Ion Transporter Protein Gene Homolog Involved in Enhanced Antibody Production.

Using the same strategy, we have successfully identified the insertion site of the GSV in the genome of another clone 263-C4G. The genomic sequence contig was taken for Blast Search in GeneBank. The genomic DNA sequence of 263-C4G shares significantly high homology with that on mouse chromosome 13, in which the ion transporter protein gene homolog (ITP) was located 15 kb downstream of the GSV insertion site. Most likely, the CMV promoter of GSV has over-expressed the ITP homolog and lead to the enhancement of antibody production in the phenotype.

Figure 17A:
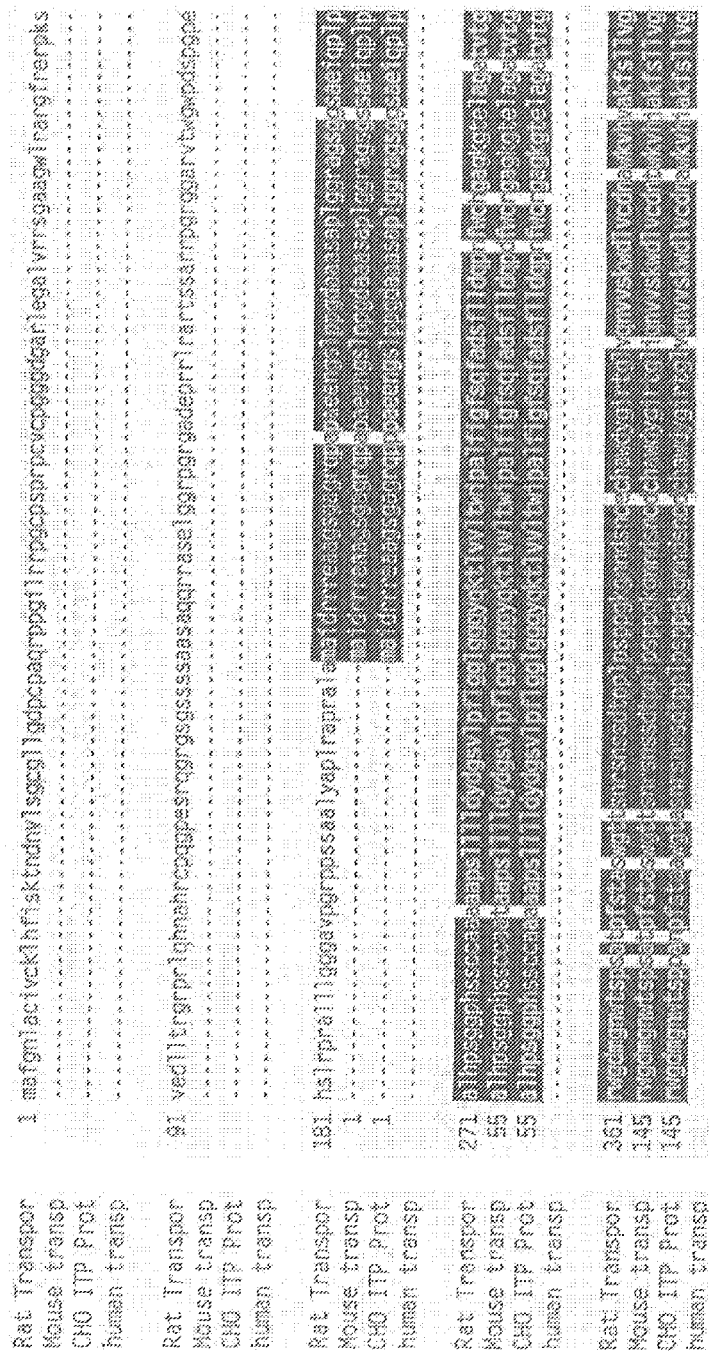
FIG. 17 is a sequence comparison for the ion transporter protein of human, rat, mouse and CHO cell, a target for RHGP pursuant to the invention.
Figure 17B:
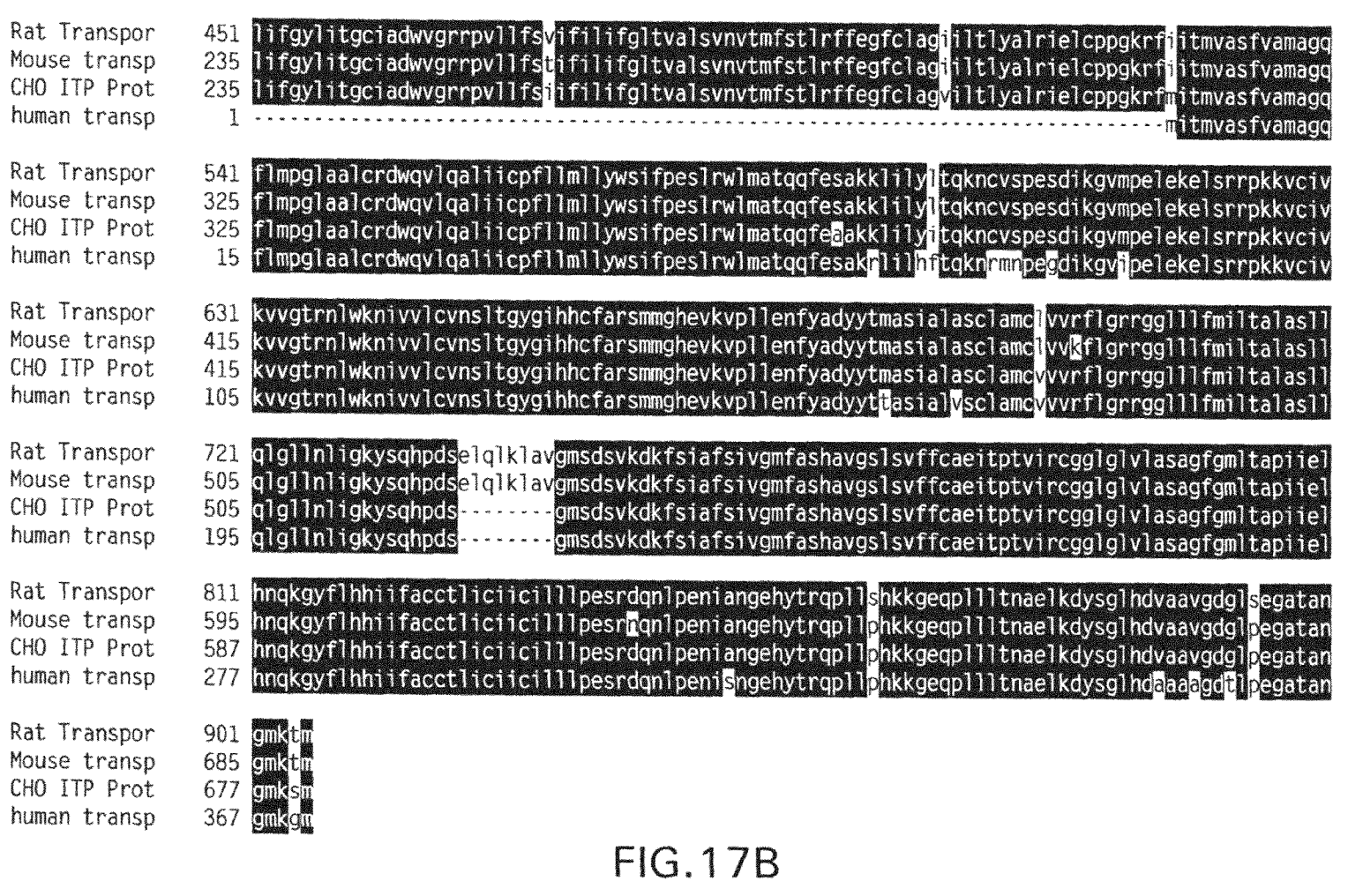

The cDNA of ITP gene was isolated by RT-PCR with mRNA of 263-C4G. The 2043-bp cDNA encodes 681 amino acids protein, which shares 96% identities with rat, and 95% with mouse and human homolog (FIG. 17). The ITP homolog belongs to the sugar-type transporter for the movement of substances such as ions, small molecules and micromolecules.

Methods—Preparation of RNA and Genomic DNA.

The total RNA was isolated from CHO cells using TIRIZOL Reagent (Invitrogen). Following the manufacturer's protocol, $5\text{-}10\times10^6$ CHO cells were used for each preparation. The mRNA was isolated using oligo dT magnetic beads (Invitrogen). To isolate the genomic DNA, the CHO cells ($5\text{-}10\times10^6$ cells) were collected and washed once with PBS solution. The cell pellet was resuspended in 10 ml of lysis buffer containing 0.32 M Sucrose, 10 mM Tris pH 7.5, 5 mM $MgCl_2$ and 1% Triton X-100. The cell lysate was centrifuged at 1500×g for 15 min. The supernatant was removed and the pellet was resuspended in 0.5 ml of proteinase K buffer containing 25 mM EDTA, 150 mM NaCl and 40 mM Tris pH 7.5 and transferred to a 1.5-ml tube. Immediately, 10 µl of 10 mg/ml proteinase K stock solution and 25 µl of 10% SDS were added to the mixture. The solution was mixed gently and incubated at 37° C. overnight. The next day, 5 µl of 10 mg/ml of RNAse A was added and incubated at 37° C. for 2-4 hrs. After RNAse A digestion, the DNA mixture was extracted twice with phenol/isoamyl alcohol/chloroform. The DNA was then precipitated with equal volume of isopropanol and centrifuged at 14000 rpm for 15 min. The pellet was washed with 70% ethanol and dissolved in 200 µl of TE (pH 7.5) buffer. The DNA concentration was determined by OD reading at $A_{260}$.

Genomic DNA Cloning.

To identify the genomic DNA sequence surrounding the GSV insertion site, 10 µg of each genomic DNA in 250 µl was digested with restriction enzyme, such as BamHI and HindIII. The digested DNA was then extracted once with phenol/isoamyl alcohol/chloroform and precipitated with 2.5 volumes of ethanol. The DNA was air dried and dissolved in 30 µl of TE buffer. The digested DNA was then self-ligated with T4 ligase at 16° C. overnight. The next day, the ligated DNA was precipitated with ethanol and dissolved in 20 µl of TE buffer. The ligated DNA was used for electroporation with ElectroMax DH10B competent cells. Sixteen colonies from each ligated DNA were grown in 1.5 ml culture for DNA preparation and digestion with the restriction enzyme for size analysis. The plasmid DNA was further analyzed by DNA sequencing.

GenBank Blast Search and Genome Mapping.

The DNA sequences were taken for mouse genome homolog search through NCBI Blast Search program. When the mouse homolog has been identified at the insertion site, the genes in that locus surrounding the GSV could be scanned and identified. The orientation of the CMV promoter in GSV will decide either the gene has been knockdown or overexpressed by RHGP. If there was no homology identified, the DNA sequencing will be continued until the mouse homolog has been found.

Construction of the CHO cDNA Library.

The cDNA library was constructed with Invitrogen's SuperScript cDNA System. Following the manufacturer's protocol, the synthesized double stranded cDNA was ligated into a vector followed by transformation with ElectroMax DH10B competent cells. Two million transformants from the electroporation mixture were used to inoculate 100 ml of the TB broth medium at 37° C. for overnight. The plasmid DNA of the library was isolated with a Qiagen kit.

PCR Amplification of ITP cDNA.

Since the exon sequence of CHO ionic transporter protein is not available, the target cDNA was amplified by PCR with degenerate primers designed from the mouse ITP homolog. A 734-bp cDNA fragment in the middle of the gene was first amplified with a pair of degenerate primers (L625: 5'AACGTGGTCAGCAARTGGGA3' SEQ ID NO:1 and R1339: 5'TTCACYTCRTGGCCCATCAT3') SEQ ID NO.2.

The amplified cDNA fragment was completely sequenced. The 5' and 3' fragments of the gene were subsequently amplified with the primers designed from the known sequences of the internal fragment combined with the 5' and 3' primers designed from the mouse ITP homolog. After the 5' and 3' fragments of the gene were amplified and sequenced, the full-length ITP cDNA was finally amplified by PCR with the primers designed from both ends of the gene (ITP-L1: 5' CCCTGGCCATGGCGATAGAY 3' SEQ ID NO.3 and C4G-R3: 5' GGTCTGTAAACCTGTGTGCA 3') SEQ ID NO.4.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. Of particular note is the fact that the expression pattern of at least one gene of a genome of a cell line expressing an antibody of interest is altered, followed by rapid screening to identify elevated SPR. Identification of candidates offering EAP, in terms of both SPR and TVP leads to expansion and stabilization of those cell lines using standard procedure, as modified for each cell line type, and in light of the modification leading to underexpression or overexpression of the targeted gene. All such modifications are intended to be within the scope of the claims appended hereto.

What is claimed is:

1. A cell line which expresses an antibody of interest, said cell line having been transformed by random homozygous gene perturbation (RHGP) to alter the expression pattern of at least one gene of the genome of said cell line other than a gene encoding said antibody through random RHGP to either increase or decrease the level of expression of said one gene, wherein said cell exhibits a specific productivity rate (SPR) for said antibody higher than that exhibited by cells of said cell line without having been transformed by RHGP and wherein said cell line transformed by RHGP comprises in its genome a gene search vector inserted in said genome during said RHGP.

2. The cell line of claim 1, wherein said cell exhibits an SPR for said antibody that is at least 1.5 times higher than that of cells of said cell line without having been transformed by RHGP.

3. The cell line of claim 2, wherein said cell exhibits an SPR for said antibody that is at least 3.0 times higher than that of cells of said cell line without having been transformed by RHGP.

4. The cell line of claim 1, wherein said expression pattern has been altered to decrease expression of said at least one gene of the genome of said cell line.

5. The cell line of claim 1, wherein said expression pattern has been altered to increase expression of said at least one gene of the genome of said cell line.

6. The cell line of claim 5, wherein said cell line is a Chinese Hamster Ovary (CHO) cell line, 293HEK cell line, HeLa cell line, COS cells, NIH3T3 cell line, Jurkat cell line, NSO cell line or HUVEC cell line.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: degenerate primer designed from the mouse ITP
      homolog

<400> SEQUENCE: 1
aacgtggtca gcaartggga                                              20

<210> SEQ ID NO 2
<211> LENGTH: 20
<212> TYPE: DNA
<213> ORGANISM: Artificial Sequence
<220> FEATURE:
<223> OTHER INFORMATION: degenerate primer designed from the mouse ITP
      homolog

<400> SEQUENCE: 2
ttcacytcrt ggcccatcat                                              20

<210> SEQ ID NO 3
<211> LENGTH: 20
<212> TYPE: DNA
<213> ORGANISM: Artificial Sequence
<220> FEATURE:
<223> OTHER INFORMATION: degenerate primer designed from the mouse ITP
      homolog

<400> SEQUENCE: 3
ccctggccat ggcgatagay                                              20
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: degenerate primer designed from the mouse ITP
      homolog

<400> SEQUENCE: 4
ggtctgtaaa cctgtgtgca                                                    20

<210> SEQ ID NO 5
<211> LENGTH: 727
<212> TYPE: PRT
<213> ORGANISM: Homo sapien

<400> SEQUENCE: 5

Met Pro Pro Pro Ala Asp Ile Val Lys Val Ala Ile Glu Trp Pro Gly
 1               5                  10                  15

Ala Tyr Pro Lys Leu Met Glu Ile Asp Gln Lys Lys Pro Leu Ser Ala
            20                  25                  30

Ile Ile Lys Glu Val Cys Asp Gly Trp Ser Leu Ala Asn His Glu Tyr
        35                  40                  45

Phe Ala Leu Gln His Ala Asp Ser Ser Asn Phe Tyr Ile Thr Glu Lys
    50                  55                  60

Asn Arg Asn Glu Ile Lys Asn Gly Thr Ile Leu Arg Leu Thr Thr Ser
65                  70                  75                  80

Pro Ala Gln Asn Ala Gln Gln Leu His Glu Arg Ile Gln Ser Ser Ser
                85                  90                  95

Met Asp Ala Lys Leu Glu Ala Leu Lys Asp Leu Ala Ser Leu Ser Arg
            100                 105                 110

Asp Val Thr Phe Ala Gln Glu Phe Ile Asn Leu Asp Gly Ile Ser Leu
        115                 120                 125

Leu Thr Gln Met Val Glu Ser Gly Thr Glu Arg Tyr Gln Lys Leu Gln
    130                 135                 140

Lys Ile Met Lys Pro Cys Phe Gly Asp Met Leu Ser Phe Thr Leu Thr
145                 150                 155                 160

Ala Phe Val Glu Leu Met Asp His Gly Ile Val Ser Trp Asp Thr Phe
                165                 170                 175

Ser Val Ala Phe Ile Lys Lys Ile Ala Ser Phe Val Asn Lys Ser Ala
            180                 185                 190

Ile Asp Ile Ser Ile Leu Gln Arg Ser Leu Ala Ile Leu Glu Ser Met
        195                 200                 205

Val Leu Asn Ser His Asp Leu Tyr Gln Lys Val Ala Gln Glu Ile Thr
    210                 215                 220

Ile Gly Gln Leu Ile Pro His Leu Gln Gly Ser Asp Gln Glu Ile Gln
225                 230                 235                 240

Thr Tyr Thr Ile Ala Val Ile Asn Ala Leu Phe Leu Lys Ala Pro Asp
                245                 250                 255

Glu Arg Arg Gln Glu Met Ala Asn Ile Leu Ala Gln Lys Gln Leu Arg
            260                 265                 270

Ser Ile Ile Leu Thr His Val Ile Arg Ala Gln Arg Ala Ile Asn Asn
        275                 280                 285

Glu Met Ala His Gln Leu Tyr Val Leu Gln Val Leu Thr Phe Asn Leu
    290                 295                 300

Leu Glu Asp Arg Met Met Thr Lys Met Asp Pro Gln Asp Gln Ala Gln
305                 310                 315                 320
```

```
Arg Asp Ile Ile Phe Glu Leu Arg Arg Ile Ala Phe Asp Ala Glu Ser
            325                 330                 335

Glu Pro Asn Asn Ser Ser Gly Ser Met Glu Lys Arg Lys Ser Met Tyr
            340                 345                 350

Thr Arg Asp Tyr Lys Lys Leu Gly Phe Ile Asn His Val Asn Pro Ala
            355                 360                 365

Met Asp Phe Thr Gln Thr Pro Pro Gly Met Leu Ala Leu Asp Asn Met
        370                 375                 380

Leu Tyr Phe Ala Lys His His Gln Asp Ala Tyr Ile Arg Ile Val Leu
385                 390                 395                 400

Glu Asn Ser Ser Arg Glu Asp Lys His Glu Cys Pro Phe Gly Arg Ser
                405                 410                 415

Ser Ile Glu Leu Thr Lys Met Leu Cys Glu Ile Leu Lys Val Gly Glu
                420                 425                 430

Leu Pro Ser Glu Thr Cys Asn Asp Phe His Pro Met Phe Phe Thr His
            435                 440                 445

Asp Arg Ser Phe Glu Glu Phe Phe Cys Ile Cys Ile Gln Leu Leu Asn
        450                 455                 460

Lys Thr Trp Lys Glu Met Arg Ala Thr Ser Glu Asp Phe Asn Lys Val
465                 470                 475                 480

Met Gln Val Val Lys Glu Gln Val Met Arg Ala Leu Thr Thr Lys Pro
                485                 490                 495

Ser Ser Leu Asp Gln Phe Lys Ser Lys Leu Gln Asn Leu Ser Tyr Thr
            500                 505                 510

Glu Ile Leu Lys Ile Arg Gln Ser Glu Arg Met Asn Gln Glu Asp Phe
        515                 520                 525

Gln Ser Arg Pro Ile Leu Glu Leu Lys Glu Lys Ile Gln Pro Glu Ile
        530                 535                 540

Leu Glu Leu Ile Lys Gln Gln Arg Leu Asn Arg Leu Val Glu Gly Thr
545                 550                 555                 560

Cys Phe Arg Lys Leu Asn Ala Arg Arg Gln Asp Lys Phe Trp Tyr
                565                 570                 575

Cys Arg Leu Ser Pro Asn His Lys Val Leu His Tyr Gly Asp Leu Glu
            580                 585                 590

Glu Ser Pro Gln Gly Glu Val Pro His Asp Ser Leu Gln Asp Lys Leu
        595                 600                 605

Pro Val Ala Asp Ile Lys Ala Val Thr Gly Lys Asp Cys Pro His
        610                 615                 620

Met Lys Glu Lys Gly Ala Leu Lys Gln Asn Lys Glu Val Leu Glu Leu
625                 630                 635                 640

Ala Phe Ser Ile Leu Tyr Asp Ser Asn Cys Gln Leu Asn Phe Ile Ala
                645                 650                 655

Pro Asp Lys His Glu Tyr Cys Ile Trp Thr Asp Gly Leu Asn Ala Leu
            660                 665                 670

Leu Gly Lys Asp Met Met Ser Asp Leu Thr Arg Asn Asp Leu Asp Thr
            675                 680                 685

Leu Leu Ser Met Glu Ile Lys Leu Arg Leu Asp Leu Glu Asn Ile
            690                 695                 700

Gln Ile Pro Asp Ala Pro Pro Ile Pro Lys Glu Pro Ser Asn Tyr
705                 710                 715                 720

Asp Phe Val Tyr Asp Cys Asn
            725

<210> SEQ ID NO 6
```

<211> LENGTH: 727
<212> TYPE: PRT
<213> ORGANISM: Mouse

<400> SEQUENCE: 6

| Met | Pro | Pro | Pro | Ser | Asp | Ile | Val | Lys | Val | Ala | Ile | Glu | Trp | Pro | Gly |
|---|---|---|---|---|---|---|---|---|---|---|---|---|---|---|---|
| 1 | | | | 5 | | | | | 10 | | | | | 15 | |

| Ala | Tyr | Pro | Lys | Leu | Met | Glu | Ile | Asp | Gln | Lys | Lys | Pro | Leu | Ser | Ala |
| | | | 20 | | | | | 25 | | | | | 30 | | |

| Ile | Ile | Lys | Glu | Val | Cys | Asp | Gly | Trp | Ser | Leu | Ala | Asn | His | Glu | Tyr |
| | | 35 | | | | | 40 | | | | | 45 | | | |

| Phe | Ala | Leu | Gln | His | Ala | Asp | Ser | Ser | Asn | Phe | Tyr | Ile | Thr | Glu | Lys |
| 50 | | | | | 55 | | | | | 60 | | | | | |

| Asn | Arg | Asn | Glu | Ile | Lys | Asn | Gly | Thr | Ile | Leu | Arg | Leu | Thr | Thr | Ser |
| 65 | | | | | 70 | | | | | 75 | | | | | 80 |

| Pro | Ala | Gln | Asn | Ala | Gln | Gln | Leu | His | Glu | Arg | Ile | Gln | Ser | Ser | Ser |
| | | | | 85 | | | | | 90 | | | | | 95 | |

| Met | Asp | Ala | Lys | Leu | Glu | Ala | Leu | Lys | Asp | Leu | Ala | Ser | Leu | Ser | Arg |
| | | | 100 | | | | | 105 | | | | | 110 | | |

| Asp | Val | Thr | Phe | Ala | Gln | Glu | Phe | Ile | Asn | Leu | Asp | Gly | Ile | Ser | Leu |
| | | 115 | | | | | 120 | | | | | 125 | | | |

| Leu | Thr | Gln | Met | Val | Glu | Ser | Gly | Thr | Glu | Arg | Tyr | Gln | Lys | Leu | Gln |
| 130 | | | | | 135 | | | | | 140 | | | | | |

| Lys | Ile | Met | Lys | Pro | Cys | Phe | Gly | Asp | Met | Leu | Ser | Phe | Thr | Leu | Thr |
| 145 | | | | | 150 | | | | | 155 | | | | | 160 |

| Ala | Phe | Val | Glu | Leu | Met | Asp | His | Gly | Ile | Val | Ser | Trp | Asp | Thr | Phe |
| | | | | 165 | | | | | 170 | | | | | 175 | |

| Ser | Val | Ala | Phe | Ile | Lys | Lys | Ile | Ala | Ser | Phe | Val | Asn | Lys | Ser | Ala |
| | | | 180 | | | | | 185 | | | | | 190 | | |

| Ile | Asp | Ile | Ser | Ile | Leu | Gln | Arg | Ser | Leu | Ala | Ile | Leu | Glu | Ser | Met |
| | | 195 | | | | | 200 | | | | | 205 | | | |

| Val | Leu | Asn | Ser | His | Asp | Leu | Tyr | Gln | Lys | Val | Ala | Gln | Glu | Ile | Thr |
| 210 | | | | | 215 | | | | | 220 | | | | | |

| Ile | Gly | Gln | Leu | Ile | Pro | His | Leu | Gln | Gly | Thr | Asp | Gln | Glu | Ile | Gln |
| 225 | | | | | 230 | | | | | 235 | | | | | 240 |

| Thr | Tyr | Thr | Ile | Ala | Val | Ile | Asn | Ala | Leu | Phe | Leu | Lys | Ala | Pro | Asp |
| | | | | 245 | | | | | 250 | | | | | 255 | |

| Glu | Arg | Arg | Gln | Glu | Met | Ala | Asn | Ile | Leu | Ala | Gln | Lys | Gln | Leu | Arg |
| | | | 260 | | | | | 265 | | | | | 270 | | |

| Tyr | Ile | Ile | Leu | Thr | His | Val | Ile | Arg | Ala | Gln | Arg | Ala | Ile | Asn | Asn |
| | | 275 | | | | | 280 | | | | | 285 | | | |

| Glu | Met | Ala | His | Gln | Leu | Tyr | Val | Leu | Gln | Val | Leu | Thr | Phe | Asn | Leu |
| 290 | | | | | 295 | | | | | 300 | | | | | |

| Leu | Glu | Asp | Arg | Met | Met | Thr | Lys | Met | Asp | Pro | Gln | Asp | Gln | Ala | Gln |
| 305 | | | | | 310 | | | | | 315 | | | | | 320 |

| Arg | Asp | Ile | Ile | Phe | Glu | Leu | Arg | Arg | Ile | Ala | Phe | Asp | Ala | Glu | Ser |
| | | | | 325 | | | | | 330 | | | | | 335 | |

| Glu | Pro | Asn | Asn | Ser | Ser | Gly | Ser | Met | Glu | Lys | Arg | Lys | Ser | Met | Tyr |
| | | | 340 | | | | | 345 | | | | | 350 | | |

| Thr | Arg | Asp | Tyr | Lys | Lys | Leu | Gly | Phe | Ile | Asn | His | Val | Asn | Pro | Ala |
| | | 355 | | | | | 360 | | | | | 365 | | | |

| Met | Asp | Phe | Thr | Gln | Thr | Pro | Pro | Gly | Met | Leu | Ala | Leu | Asp | Asn | Met |
| 370 | | | | | 375 | | | | | 380 | | | | | |

| Leu | Tyr | Phe | Ala | Lys | His | His | Gln | Asp | Ala | Tyr | Ile | Arg | Ile | Val | Leu |
| 385 | | | | | 390 | | | | | 395 | | | | | 400 |

```
Glu Asn Ser Ser Arg Glu Asp Lys His Glu Cys Pro Phe Gly Arg Ser
            405                 410                 415

Ser Ile Glu Leu Thr Lys Met Leu Cys Glu Ile Leu Lys Val Gly Glu
        420                 425                 430

Leu Pro Ser Glu Thr Cys Asn Asp Phe His Pro Met Phe Phe Thr His
        435                 440                 445

Asp Arg Ser Phe Glu Phe Phe Cys Ile Cys Ile Gln Leu Leu Asn
450                 455                 460

Lys Thr Trp Lys Glu Met Arg Ala Thr Ser Glu Asp Phe Asn Lys Val
465                 470                 475                 480

Met Gln Val Val Lys Glu Gln Val Met Arg Ala Leu Thr Thr Lys Pro
                485                 490                 495

Ser Ser Leu Asp Gln Phe Lys Ser Lys Leu Gln Asn Leu Ser Tyr Thr
                500                 505                 510

Glu Ile Leu Lys Ile Arg Gln Ser Glu Arg Met Asn Gln Glu Asp Phe
            515                 520                 525

Gln Ser Arg Pro Ile Leu Glu Leu Lys Glu Lys Ile Gln Pro Glu Ile
530                 535                 540

Leu Glu Leu Ile Lys Gln Gln Arg Leu Asn Arg Leu Val Glu Gly Thr
545                 550                 555                 560

Cys Phe Arg Lys Leu Asn Ala Arg Arg Gln Asp Lys Phe Trp Tyr
                565                 570                 575

Cys Arg Leu Ser Pro Asn His Lys Val Leu His Tyr Gly Asp Leu Glu
                580                 585                 590

Glu Ser Pro Gln Gly Glu Val Pro His Asp Ser Leu Gln Asp Lys Leu
            595                 600                 605

Pro Val Ala Asp Ile Lys Ala Val Val Thr Gly Lys Asp Cys Pro His
        610                 615                 620

Met Lys Glu Lys Gly Ala Leu Lys Gln Asn Lys Glu Val Leu Glu Leu
625                 630                 635                 640

Ala Phe Ser Ile Leu Tyr Asp Ser Asn Cys Gln Leu Asn Phe Ile Ala
                645                 650                 655

Pro Asp Lys His Glu Tyr Cys Ile Trp Thr Asp Gly Leu Asn Ala Leu
                660                 665                 670

Leu Gly Lys Asp Met Met Ser Asp Leu Thr Arg Asn Asp Leu Asp Thr
            675                 680                 685

Leu Leu Ser Met Glu Ile Lys Leu Arg Leu Leu Asp Leu Glu Asn Ile
        690                 695                 700

Gln Ile Pro Asp Ala Pro Pro Ile Pro Lys Glu Pro Ser Asn Tyr
705                 710                 715                 720

Asp Phe Val Tyr Asp Cys Asn
                725

<210> SEQ ID NO 7
<211> LENGTH: 727
<212> TYPE: PRT
<213> ORGANISM: Rat

<400> SEQUENCE: 7

Met Pro Pro Pro Ser Asp Ile Val Lys Val Ala Ile Glu Trp Pro Gly
1               5                   10                  15

Ala Tyr Pro Lys Leu Met Glu Ile Asp Gln Lys Lys Pro Leu Ser Ala
            20                  25                  30

Ile Ile Lys Glu Val Cys Asp Gly Trp Ser Leu Ala Asn His Glu Tyr
        35                  40                  45
```

```
Phe Ala Leu Gln His Ala Asp Ser Ser Asn Phe Tyr Ile Thr Glu Lys
     50                  55                  60

Asn Arg Asn Glu Ile Lys Asn Gly Thr Ile Leu Arg Leu Thr Thr Ser
 65                  70                  75                  80

Pro Ala Gln Asn Ala Gln Gln Leu His Glu Arg Ile Gln Ser Ser Ser
                 85                  90                  95

Met Asp Ala Lys Leu Glu Ala Leu Lys Asp Leu Ala Ser Leu Ser Arg
            100                 105                 110

Asp Val Thr Phe Ala Gln Glu Phe Ile Asn Leu Asp Gly Ile Ser Leu
            115                 120                 125

Leu Thr Gln Met Val Glu Ser Gly Thr Glu Arg Tyr Gln Lys Leu Gln
    130                 135                 140

Lys Ile Met Lys Pro Cys Phe Gly Asp Met Leu Ser Phe Thr Leu Thr
145                 150                 155                 160

Ala Phe Val Glu Leu Met Asp His Gly Ile Val Ser Trp Asp Thr Phe
                165                 170                 175

Ser Val Ala Phe Ile Lys Lys Ile Ala Ser Phe Val Asn Lys Ser Ala
            180                 185                 190

Ile Asp Ile Ser Ile Leu Gln Arg Ser Leu Ala Ile Leu Glu Ser Met
            195                 200                 205

Val Leu Asn Ser His Asp Leu Tyr Gln Lys Val Ala Gln Glu Ile Thr
    210                 215                 220

Ile Gly Gln Leu Ile Pro His Leu Gln Gly Thr Asp Gln Glu Ile Gln
225                 230                 235                 240

Thr Tyr Thr Ile Ala Val Ile Asn Ala Leu Phe Leu Lys Ala Pro Asp
                245                 250                 255

Glu Arg Arg Gln Glu Met Ala Asn Ile Leu Ala Gln Lys Gln Leu Arg
            260                 265                 270

Tyr Ile Ile Leu Thr His Val Ile Arg Ala Gln Arg Ala Ile Asn Asn
            275                 280                 285

Glu Met Ala His Gln Leu Tyr Val Leu Gln Val Leu Thr Phe Asn Leu
    290                 295                 300

Leu Glu Asp Arg Met Met Thr Lys Met Asp Pro Gln Asp Gln Ala Gln
305                 310                 315                 320

Arg Asp Ile Ile Phe Glu Leu Arg Arg Ile Ala Phe Asp Ala Glu Ser
                325                 330                 335

Glu Pro Asn Asn Ser Ser Gly Ser Met Glu Lys Arg Lys Ser Met Tyr
            340                 345                 350

Thr Arg Asp Tyr Lys Lys Leu Gly Phe Ile Asn His Val Asn Pro Ala
            355                 360                 365

Met Asp Phe Thr Gln Thr Pro Pro Gly Met Leu Ala Leu Asp Asn Met
    370                 375                 380

Leu Tyr Phe Ala Lys His His Gln Asp Ala Tyr Ile Arg Ile Val Leu
385                 390                 395                 400

Glu Asn Ser Ser Arg Glu Asp Lys His Glu Cys Pro Phe Gly Arg Ser
                405                 410                 415

Ser Ile Glu Leu Thr Lys Met Leu Cys Glu Ile Leu Lys Val Gly Glu
            420                 425                 430

Leu Pro Ser Glu Thr Cys Asn Asp Phe His Pro Met Phe Phe Thr His
            435                 440                 445

Asp Arg Ser Phe Glu Gly Phe Phe Cys Ile Cys Ile Gln Leu Leu Asn
    450                 455                 460

Lys Thr Trp Lys Glu Met Arg Ala Thr Ser Glu Asp Phe Asn Lys Val
```

```
                    465                 470                 475                 480
        Met Gln Val Val Lys Glu Gln Val Met Arg Ala Leu Thr Thr Lys Pro
                            485                 490                 495

Ser Ser Leu Asp Gln Phe Lys Ser Lys Leu Gln Asn Leu Ser Tyr Thr
                        500                 505                 510

Glu Ile Leu Lys Ile Arg Gln Ser Glu Arg Met Asn Gln Glu Asp Phe
                    515                 520                 525

Gln Ser Arg Pro Ile Leu Glu Leu Lys Glu Lys Ile Gln Pro Glu Ile
                    530                 535                 540

Leu Glu Leu Ile Lys Gln Gln Arg Leu Asn Arg Leu Val Glu Gly Thr
        545                 550                 555                 560

Cys Phe Arg Lys Leu Asn Ala Arg Arg Gln Asp Lys Phe Trp Tyr
                            565                 570                 575

Cys Arg Leu Ser Pro Asn His Lys Val Leu His Tyr Gly Asp Leu Glu
                        580                 585                 590

Glu Ser Pro Gln Gly Glu Val Pro His Asp Ser Leu Gln Asp Lys Leu
                        595                 600                 605

Pro Val Ala Asp Ile Lys Ala Val Val Thr Gly Lys Asp Cys Pro His
                    610                 615                 620

Met Lys Glu Lys Gly Ala Leu Lys Gln Asn Lys Glu Val Leu Glu Leu
        625                 630                 635                 640

Ala Phe Ser Ile Leu Tyr Asp Ser Asn Cys Gln Leu Asn Phe Ile Ala
                            645                 650                 655

Pro Asp Lys His Glu Tyr Cys Ile Trp Thr Asp Gly Leu Asn Ala Leu
                        660                 665                 670

Leu Gly Lys Asp Met Met Ser Asp Leu Thr Arg Asn Asp Leu Asp Thr
                    675                 680                 685

Leu Leu Ser Met Glu Ile Lys Leu Arg Leu Leu Asp Leu Glu Asn Ile
                690                 695                 700

Gln Ile Pro Asp Ala Pro Pro Ile Pro Lys Glu Pro Ser Asn Tyr
        705                 710                 715                 720

Asp Phe Val Tyr Asp Cys Asn
                    725

<210> SEQ ID NO 8
<211> LENGTH: 727
<212> TYPE: PRT
<213> ORGANISM: Chinese Hampster

<400> SEQUENCE: 8

Met Pro Pro Pro Ser Asp Ile Val Lys Val Ala Ile Glu Trp Pro Gly
        1                   5                   10                  15

Ala Tyr Pro Lys Leu Met Glu Ile Asp Gln Lys Lys Pro Leu Ser Ala
                        20                  25                  30

Ile Ile Lys Glu Val Cys Asp Gly Trp Ser Leu Ala Asn His Glu Tyr
                    35                  40                  45

Phe Ala Leu Gln His Ala Asp Ser Ser Asn Phe Tyr Ile Thr Glu Lys
                50                  55                  60

Asn Arg Asn Glu Ile Lys Asn Gly Thr Ile Leu Arg Leu Thr Thr Ser
        65                  70                  75                  80

Pro Ala Gln Asn Ala Gln Gln Leu His Glu Arg Ile Gln Ser Ser Ser
                            85                  90                  95

Met Asp Ala Lys Leu Glu Ala Leu Lys Asp Leu Ala Ser Leu Ser Arg
                        100                 105                 110

Asp Val Thr Phe Ala Gln Glu Phe Ile Asn Leu Asp Gly Ile Ser Leu
```

-continued

```
            115                 120                 125
Leu Thr Gln Met Val Glu Ser Gly Thr Glu Arg Tyr Gln Lys Leu Gln
130                 135                 140
Lys Ile Met Lys Pro Cys Phe Gly Asp Met Leu Ser Phe Thr Leu Thr
145                 150                 155                 160
Ala Phe Val Glu Leu Met Asp His Gly Ile Val Ser Trp Asp Thr Phe
                165                 170                 175
Ser Val Ala Phe Ile Lys Lys Ile Ala Ser Phe Val Asn Lys Ser Ala
                180                 185                 190
Ile Asp Ile Ser Ile Leu Gln Arg Ser Leu Ala Ile Leu Glu Ser Met
                195                 200                 205
Val Leu Asn Ser His Asp Leu Tyr Gln Lys Val Ala Gln Glu Ile Thr
210                 215                 220
Ile Gly Gln Leu Ile Pro His Leu Gln Gly Thr Asp Gln Glu Ile Gln
225                 230                 235                 240
Thr Tyr Thr Ile Ala Val Ile Asn Ala Leu Phe Leu Lys Ala Pro Asp
                245                 250                 255
Glu Arg Arg Gln Glu Met Ala Asn Ile Leu Ala Gln Lys Gln Leu Arg
                260                 265                 270
Tyr Ile Ile Leu Thr His Val Ile Arg Ala Gln Arg Ala Ile Asn Asn
                275                 280                 285
Glu Met Ala His Gln Leu Tyr Val Leu Gln Val Leu Thr Phe Asn Leu
                290                 295                 300
Leu Glu Asp Arg Met Met Thr Lys Met Asp Pro Gln Asp Gln Ala Gln
305                 310                 315                 320
Arg Asp Ile Ile Phe Glu Leu Arg Arg Ile Ala Phe Asp Ala Glu Leu
                325                 330                 335
Glu Pro Asn Asn Ser Ser Gly Ser Met Glu Lys Arg Lys Ser Met Tyr
                340                 345                 350
Thr Arg Asp Tyr Lys Lys Leu Gly Phe Ile Asn His Val Asn Pro Ala
                355                 360                 365
Met Asp Phe Thr Gln Thr Pro Pro Gly Met Leu Ala Leu Asp Asn Met
370                 375                 380
Leu Tyr Phe Ala Lys His His Gln Asp Ala Tyr Ile Arg Ile Val Leu
385                 390                 395                 400
Glu Asn Ser Ser Arg Glu Asp Lys His Glu Cys Pro Phe Gly Arg Ser
                405                 410                 415
Ser Ile Glu Leu Thr Lys Met Leu Cys Glu Ile Leu Lys Val Gly Glu
                420                 425                 430
Leu Pro Ser Glu Thr Cys Asn Asp Phe His Pro Met Phe Phe Thr His
                435                 440                 445
Asp Arg Ser Phe Glu Glu Phe Phe Cys Ile Cys Ile Gln Leu Leu Asn
                450                 455                 460
Lys Thr Trp Lys Glu Met Arg Ala Thr Ser Glu Asp Phe Asn Lys Val
465                 470                 475                 480
Met Gln Val Val Lys Glu Gln Val Met Arg Ala Leu Thr Thr Lys Pro
                485                 490                 495
Ser Ser Leu Asp Gln Phe Lys Ser Lys Leu Gln Asn Leu Ser Tyr Thr
                500                 505                 510
Glu Ile Leu Lys Ile Arg Gln Ser Glu Arg Met Asn Gln Glu Asp Phe
                515                 520                 525
Gln Ser Arg Pro Ile Leu Glu Leu Lys Glu Lys Ile Gln Pro Glu Ile
530                 535                 540
```

```
Leu Glu Leu Ile Lys Gln Gln Arg Leu Asn Arg Leu Val Glu Gly Thr
545                 550                 555                 560

Cys Phe Arg Lys Leu Asn Ala Arg Arg Arg Gln Asp Lys Phe Trp Tyr
                565                 570                 575

Cys Arg Leu Ser Pro Asn His Lys Val Leu His Tyr Gly Asp Leu Glu
            580                 585                 590

Glu Ser Pro Gln Gly Glu Val Pro His Asp Ser Leu Gln Asp Lys Leu
        595                 600                 605

Pro Val Ala Asp Ile Lys Ala Val Thr Gly Lys Asp Cys Pro His
    610                 615                 620

Met Lys Glu Lys Gly Ala Leu Lys Gln Asn Lys Glu Val Leu Glu Leu
625                 630                 635                 640

Ala Phe Ser Ile Leu Tyr Asp Ser Asn Cys Gln Leu Asn Phe Ile Ala
                645                 650                 655

Pro Asp Lys His Glu Tyr Cys Ile Trp Thr Asp Gly Leu Asn Ala Leu
            660                 665                 670

Leu Gly Lys Asp Met Leu Ser Asp Leu Thr Arg Asn Asp Leu Asp Thr
        675                 680                 685

Leu Leu Ser Met Glu Ile Lys Leu Arg Leu Leu Asp Leu Glu Asn Ile
690                 695                 700

Gln Ile Pro Asp Ala Pro Pro Ile Pro Lys Glu Pro Ser Asn Tyr
705                 710                 715                 720

Asp Phe Val Tyr Asp Cys Asn
                725

<210> SEQ ID NO 9
<211> LENGTH: 905
<212> TYPE: PRT
<213> ORGANISM: Rat

<400> SEQUENCE: 9

Met Ala Phe Gly Asn Leu Ala Cys Ile Val Cys Lys Leu His Phe Ile
1               5                   10                  15

Ser Lys Thr Asn Asp Asn Val Leu Ser Gly Cys Gly Leu Leu Gly Asp
                20                  25                  30

Pro Cys Pro Ala Gln Arg Pro Gly Ile Leu Arg Arg Pro Gly Cys
            35                  40                  45

Pro Ser Pro Arg Pro Cys Val Cys Pro Gly Gly Asp Gly Ala Arg
        50                  55                  60

Leu Glu Gly Ala Leu Val Arg Arg Ser Gly Ala Ala Gly Trp Leu Arg
65                  70                  75                  80

Ala Arg Gly Phe Arg Glu Arg Pro Lys Ser Val Glu Asp Leu Leu Thr
                85                  90                  95

Arg Gly Arg Pro Arg Leu Gln His Asn Ala His Arg Cys Pro Gln Gly
            100                 105                 110

Pro Glu Ser Arg Gln Gly Arg Gly Ser Gly Ser Ser Ser Ala Ala
        115                 120                 125

Ser Ala Gln Gln Arg Arg Ala Ser Glu Leu Gly Gly Arg Pro Gly Arg
130                 135                 140

Gly Ala Asp Glu Pro Arg Arg Leu Arg Ala Arg Thr Ser Ser Ala Arg
145                 150                 155                 160

Arg Pro Gly Arg Gly Gly Ala Arg Val Thr Trp Gly Trp Pro Asp Ser
                165                 170                 175

Pro Gly Pro Glu His Ser Leu Arg Pro Arg Ala Leu Leu Leu Gly Gly
            180                 185                 190
```

-continued

```
Gly Ala Val Pro Gly Arg Pro Pro Ser Ser Ala Ala Leu Tyr Ala Pro
            195                 200                 205

Leu Arg Ala Pro Arg Ala Leu Ala Met Ala Ile Asp Arg Arg Arg Glu
            210                 215                 220

Ala Ala Gly Ser Gly Ala Gly Arg Gln Pro Ala Pro Ala Glu Glu Asn
225                 230                 235                 240

Gly Ser Leu Pro Pro Gly Asp Ala Ala Ser Ala Pro Leu Gly Gly
            245                 250                 255

Arg Ala Gly Ser Gly Gly Ser Ala Glu Ile Gln Pro Leu Pro Ala Leu
            260                 265                 270

His Pro Ser Gly Gly Pro His Ser Ser Cys Ala Ala Ala Ala
            275                 280                 285

Pro Ser Leu Leu Leu Leu Asp Tyr Asp Gly Ser Val Leu Pro Phe Leu
            290                 295                 300

Gly Gly Leu Gly Gly Gly Tyr Gln Lys Thr Leu Val Val Leu Thr Trp
305                 310                 315                 320

Ile Pro Ala Leu Phe Ile Gly Phe Ser Gln Phe Ser Asp Ser Phe Leu
            325                 330                 335

Leu Asp Gln Pro Asn Phe Trp Cys His Gly Ala Gly Lys Gly Thr Glu
            340                 345                 350

Leu Ala Gly Ala Thr Val Thr Gly Arg Trp Gly Asp Met Gly Asn Trp
            355                 360                 365

Thr Ser Pro Ser Ala Thr Pro Phe Ser Thr Ala Ser Trp Gly Thr Thr
370                 375                 380

Ser Asn Arg Ser Asn Ser Ser Asp Thr Pro Pro Leu Pro Ser Pro Pro
385                 390                 395                 400

Gly Lys Gly Asn Asn Asp Ser Asn Cys Glu Cys His Ala Trp Asp Tyr
            405                 410                 415

Gly Ile Arg Thr Gly Leu Val Gln Asn Val Val Ser Lys Trp Asp Leu
            420                 425                 430

Val Cys Asp Asn Ala Trp Lys Val His Val Ala Lys Phe Ser Leu Leu
            435                 440                 445

Val Gly Leu Ile Phe Gly Tyr Leu Ile Thr Gly Cys Ile Ala Asp Trp
450                 455                 460

Val Gly Arg Arg Pro Val Leu Leu Phe Ser Val Ile Phe Ile Leu Ile
465                 470                 475                 480

Phe Gly Leu Thr Val Ala Leu Ser Val Asn Val Thr Met Phe Ser Thr
            485                 490                 495

Leu Arg Phe Phe Glu Gly Phe Cys Leu Ala Gly Ile Ile Leu Thr Leu
            500                 505                 510

Tyr Ala Leu Arg Ile Glu Leu Cys Pro Pro Gly Lys Arg Phe Ile Ile
            515                 520                 525

Thr Met Val Ala Ser Phe Val Ala Met Ala Gly Gln Phe Leu Met Pro
530                 535                 540

Gly Leu Ala Ala Leu Cys Arg Asp Trp Gln Val Leu Gln Ala Leu Ile
545                 550                 555                 560

Ile Cys Pro Phe Leu Leu Met Leu Leu Tyr Trp Ser Ile Phe Pro Glu
            565                 570                 575

Ser Leu Arg Trp Leu Met Ala Thr Gln Gln Phe Glu Ser Ala Lys Lys
            580                 585                 590

Leu Ile Leu Tyr Leu Thr Gln Lys Asn Cys Val Ser Pro Glu Ser Asp
            595                 600                 605

Ile Lys Gly Val Met Pro Glu Leu Glu Lys Glu Leu Ser Arg Arg Pro
            610                 615                 620
```

```
Lys Lys Val Cys Ile Val Lys Val Val Gly Thr Arg Asn Leu Trp Lys
625                 630                 635                 640

Asn Ile Val Val Leu Cys Val Asn Ser Leu Thr Gly Tyr Gly Ile His
                645                 650                 655

His Cys Phe Ala Arg Ser Met Met Gly His Glu Val Lys Val Pro Leu
            660                 665                 670

Leu Glu Asn Phe Tyr Ala Asp Tyr Tyr Thr Thr Ala Ser Ile Ala Leu
        675                 680                 685

Val Ser Cys Leu Ala Met Cys Val Val Arg Phe Leu Gly Arg Arg
690                 695                 700

Gly Gly Leu Leu Leu Phe Met Ile Leu Thr Ala Leu Ala Ser Leu Leu
705                 710                 715                 720

Gln Leu Gly Leu Leu Asn Leu Ile Gly Lys Tyr Ser Gln His Pro Asp
                725                 730                 735

Ser Glu Leu Gln Leu Lys Leu Ala Val Gly Met Ser Asp Ser Val Lys
            740                 745                 750

Asp Lys Phe Ser Ile Ala Phe Ser Ile Val Gly Met Phe Ala Ser His
        755                 760                 765

Ala Val Gly Ser Leu Ser Val Phe Phe Cys Ala Glu Ile Thr Pro Thr
770                 775                 780

Val Ile Arg Cys Gly Gly Leu Gly Leu Val Leu Ala Ser Ala Gln Phe
785                 790                 795                 800

Gly Met Leu Thr Ala Pro Ile Ile Glu Leu His Asn Gln Lys Gly Tyr
                805                 810                 815

Phe Leu His His Ile Ile Phe Ala Cys Cys Thr Leu Ile Cys Ile Ile
            820                 825                 830

Cys Ile Leu Leu Leu Pro Glu Ser Arg Asp Gln Asn Leu Pro Glu Asn
        835                 840                 845

Ile Ala Asn Gly Glu His Tyr Thr Arg Gln Pro Leu Leu Ser His Lys
850                 855                 860

Lys Gly Glu Gln Pro Leu Leu Leu Thr Asn Ala Glu Leu Lys Asp Tyr
865                 870                 875                 880

Ser Gly Leu His Asp Val Ala Ala Val Gly Asp Gly Leu Ser Glu Gly
                885                 890                 895

Ala Thr Ala Asn Gly Met Lys Thr Met
            900                 905

<210> SEQ ID NO 10
<211> LENGTH: 689
<212> TYPE: PRT
<213> ORGANISM: Mouse

<400> SEQUENCE: 10

Met Ala Ile Asp Arg Arg Arg Glu Ala Ala Gly Ser Gly Ala Gly Arg
1               5                   10                  15

Gln Pro Ala Pro Ala Glu Glu Asn Gly Ser Leu Pro Gly Asp Ala
            20                  25                  30

Ala Ala Ser Ala Pro Leu Gly Gly Arg Ala Gly Ser Gly Gly Ser Ala
        35                  40                  45

Glu Ile Gln Pro Leu Pro Ala Leu His Pro Ser Gly Gly Pro His Ser
    50                  55                  60

Ser Cys Cys Ala Ala Ala Ala Pro Ser Leu Leu Leu Asp Tyr
65                  70                  75                  80

Asp Gly Ser Val Leu Pro Phe Leu Gly Gly Leu Gly Gly Gly Tyr Gln
                85                  90                  95
```

```
Lys Thr Leu Val Val Leu Thr Trp Ile Pro Ala Leu Phe Ile Gly Phe
            100                 105                 110

Ser Gln Phe Ser Asp Ser Phe Leu Asp Gln Pro Asn Phe Trp Cys
        115                 120                 125

His Gly Ala Gly Lys Gly Thr Glu Leu Ala Gly Ala Thr Val Thr Gly
    130                 135                 140

Arg Trp Gly Asp Met Gly Asn Trp Thr Ser Pro Ser Ala Thr Pro Phe
145                 150                 155                 160

Ser Thr Ala Ser Trp Gly Thr Thr Ser Asn Arg Ser Asn Ser Ser Asp
                165                 170                 175

Thr Pro Pro Leu Pro Ser Pro Gly Lys Gly Asn Asn Asp Ser Asn
            180                 185                 190

Cys Glu Cys His Ala Trp Asp Tyr Gly Ile Arg Thr Gly Leu Val Gln
            195                 200                 205

Asn Val Val Ser Lys Trp Asp Leu Val Cys Asp Asn Ala Trp Lys Val
        210                 215                 220

His Val Ala Lys Phe Ser Leu Leu Val Gly Leu Ile Phe Gly Tyr Leu
225                 230                 235                 240

Ile Thr Gly Cys Ile Ala Asp Trp Val Gly Arg Pro Val Leu Leu
            245                 250                 255

Phe Ser Val Ile Phe Ile Leu Ile Phe Gly Leu Thr Val Ala Leu Ser
                260                 265                 270

Val Asn Val Thr Met Phe Ser Thr Leu Arg Phe Phe Glu Gly Phe Cys
        275                 280                 285

Leu Ala Gly Ile Ile Leu Thr Leu Tyr Ala Leu Arg Ile Glu Leu Cys
        290                 295                 300

Pro Pro Gly Lys Arg Phe Met Ile Thr Met Val Ala Ser Phe Val Ala
305                 310                 315                 320

Met Ala Gly Gln Phe Leu Met Pro Gly Leu Ala Ala Leu Cys Arg Asp
                325                 330                 335

Trp Gln Val Leu Gln Ala Leu Ile Ile Cys Pro Phe Leu Leu Met Leu
            340                 345                 350

Leu Tyr Trp Ser Ile Phe Pro Glu Ser Leu Arg Trp Leu Met Ala Thr
        355                 360                 365

Gln Gln Phe Glu Ser Ala Lys Lys Leu Ile Leu Tyr Leu Thr Gln Lys
        370                 375                 380

Asn Cys Val Ser Pro Glu Ser Asp Ile Lys Gly Val Met Pro Glu Leu
385                 390                 395                 400

Glu Lys Glu Leu Ser Arg Arg Pro Lys Lys Val Cys Ile Val Lys Val
                405                 410                 415

Val Gly Thr Arg Asn Leu Trp Lys Asn Ile Val Val Leu Cys Val Asn
            420                 425                 430

Ser Leu Thr Gly Tyr Gly Ile His His Cys Phe Ala Arg Ser Met Met
        435                 440                 445

Gly His Glu Val Lys Val Pro Leu Leu Glu Asn Phe Tyr Ala Asp Tyr
    450                 455                 460

Tyr Thr Thr Ala Ser Ile Ala Leu Val Ser Cys Leu Ala Met Cys Val
465                 470                 475                 480

Val Val Arg Phe Leu Gly Arg Arg Gly Leu Leu Leu Phe Met Ile
                485                 490                 495

Leu Thr Ala Leu Ala Ser Leu Leu Gln Leu Gly Leu Leu Asn Leu Ile
            500                 505                 510

Gly Lys Tyr Ser Gln His Pro Asp Ser Glu Leu Gln Leu Lys Leu Ala
```

```
                    515                 520                 525
Val Gly Met Ser Asp Ser Val Lys Asp Lys Phe Ser Ile Ala Phe Ser
    530                 535                 540

Ile Val Gly Met Phe Ala Ser His Ala Val Gly Ser Leu Ser Val Phe
545                 550                 555                 560

Phe Cys Ala Glu Ile Thr Pro Thr Val Ile Arg Cys Gly Gly Leu Gly
                565                 570                 575

Leu Val Leu Ala Ser Ala Gln Phe Gly Met Leu Thr Ala Pro Ile Ile
            580                 585                 590

Glu Leu His Asn Gln Lys Gly Tyr Phe Leu His His Ile Ile Phe Ala
        595                 600                 605

Cys Cys Thr Leu Ile Cys Ile Ile Cys Ile Leu Leu Leu Pro Glu Ser
    610                 615                 620

Arg Asp Gln Asn Leu Pro Glu Asn Ile Ala Asn Gly Glu His Tyr Thr
625                 630                 635                 640

Arg Gln Pro Leu Leu Ser His Lys Lys Gly Glu Gln Pro Leu Leu Leu
                645                 650                 655

Thr Asn Ala Glu Leu Lys Asp Tyr Ser Gly Leu His Asp Val Ala Ala
            660                 665                 670

Val Gly Asp Gly Leu Ser Glu Gly Ala Thr Ala Asn Gly Met Lys Ser
        675                 680                 685

Met

<210> SEQ ID NO 11
<211> LENGTH: 681
<212> TYPE: PRT
<213> ORGANISM: Chinese Hampster

<400> SEQUENCE: 11

Met Ala Ile Asp Arg Arg Glu Ala Ala Gly Ser Gly Ala Gly Arg
  1               5                  10                  15

Gln Pro Ala Pro Ala Glu Glu Asn Gly Ser Leu Pro Pro Gly Asp Ala
                 20                  25                  30

Ala Ala Ser Ala Pro Leu Gly Gly Arg Ala Gly Ser Gly Gly Ser Ala
             35                  40                  45

Glu Ile Gln Pro Leu Pro Ala Leu His Pro Ser Gly Gly Pro His Ser
 50                  55                  60

Ser Cys Cys Ala Ala Ala Ala Pro Ser Leu Leu Leu Asp Tyr
 65                  70                  75                  80

Asp Gly Ser Val Leu Pro Phe Leu Gly Gly Leu Gly Gly Tyr Gln
                 85                  90                  95

Lys Thr Leu Val Val Leu Thr Trp Ile Pro Ala Leu Phe Ile Gly Phe
            100                 105                 110

Ser Gln Phe Ser Asp Ser Phe Leu Leu Asp Gln Pro Asn Phe Trp Cys
        115                 120                 125

His Gly Ala Gly Lys Gly Thr Glu Leu Ala Gly Ala Thr Val Thr Gly
    130                 135                 140

Arg Trp Gly Asp Met Gly Asn Trp Thr Ser Pro Ser Ala Thr Pro Phe
145                 150                 155                 160

Ser Thr Ala Ser Trp Gly Thr Thr Ser Asn Arg Ser Asn Ser Ser Asp
                165                 170                 175

Thr Pro Pro Leu Pro Ser Pro Gly Lys Gly Asn Asn Asp Ser Asn
            180                 185                 190

Cys Glu Cys His Ala Trp Asp Tyr Gly Ile Arg Thr Gly Leu Val Gln
        195                 200                 205
```

```
Asn Val Val Ser Lys Trp Asp Leu Val Cys Asp Asn Ala Trp Lys Val
    210                 215                 220

His Val Ala Lys Phe Ser Leu Leu Val Gly Leu Ile Phe Gly Tyr Leu
225                 230                 235                 240

Ile Thr Gly Cys Ile Ala Asp Trp Val Gly Arg Arg Pro Val Leu Leu
                245                 250                 255

Phe Ser Val Ile Phe Ile Leu Ile Phe Gly Leu Thr Val Ala Leu Ser
                260                 265                 270

Val Asn Val Thr Met Phe Ser Thr Leu Arg Phe Phe Glu Gly Phe Cys
            275                 280                 285

Leu Ala Gly Ile Ile Leu Thr Leu Tyr Ala Leu Arg Ile Glu Leu Cys
    290                 295                 300

Pro Pro Gly Lys Arg Phe Met Ile Thr Met Val Ala Ser Phe Val Ala
305                 310                 315                 320

Met Ala Gly Gln Phe Leu Met Pro Gly Leu Ala Ala Leu Cys Arg Asp
                325                 330                 335

Trp Gln Val Leu Gln Ala Leu Ile Ile Cys Pro Phe Leu Leu Met Leu
                340                 345                 350

Leu Tyr Trp Ser Ile Phe Pro Glu Ser Leu Arg Trp Leu Met Ala Thr
            355                 360                 365

Gln Gln Phe Glu Ser Ala Lys Lys Leu Ile Leu Tyr Leu Thr Gln Lys
    370                 375                 380

Asn Cys Val Ser Pro Glu Ser Asp Ile Lys Gly Val Met Pro Glu Leu
385                 390                 395                 400

Glu Lys Glu Leu Ser Arg Arg Pro Lys Lys Val Cys Ile Val Lys Val
                405                 410                 415

Val Gly Thr Arg Asn Leu Trp Lys Asn Ile Val Val Leu Cys Val Asn
                420                 425                 430

Ser Leu Thr Gly Tyr Gly Ile His His Cys Phe Ala Arg Ser Met Met
            435                 440                 445

Gly His Glu Val Lys Val Pro Leu Leu Glu Asn Phe Tyr Ala Asp Tyr
    450                 455                 460

Tyr Thr Thr Ala Ser Ile Ala Leu Val Ser Cys Leu Ala Met Cys Val
465                 470                 475                 480

Val Val Arg Phe Leu Gly Arg Arg Gly Gly Leu Leu Leu Phe Met Ile
                485                 490                 495

Leu Thr Ala Leu Ala Ser Leu Leu Gln Leu Gly Leu Leu Asn Leu Ile
                500                 505                 510

Gly Lys Tyr Ser Gln His Pro Asp Ser Gly Met Ser Asp Ser Val Lys
            515                 520                 525

Asp Lys Phe Ser Ile Ala Phe Ser Ile Val Gly Met Phe Ala Ser His
    530                 535                 540

Ala Val Gly Ser Leu Ser Val Phe Phe Cys Ala Glu Ile Thr Pro Thr
545                 550                 555                 560

Val Ile Arg Cys Gly Gly Leu Gly Leu Val Leu Ala Ser Ala Gln Phe
                565                 570                 575

Gly Met Leu Thr Ala Pro Ile Ile Glu Leu His Asn Gln Lys Gly Tyr
                580                 585                 590

Phe Leu His His Ile Ile Phe Ala Cys Cys Thr Leu Ile Cys Ile Ile
            595                 600                 605

Cys Ile Leu Leu Leu Pro Glu Ser Arg Asp Gln Asn Leu Pro Glu Asn
    610                 615                 620

Ile Ala Asn Gly Glu His Tyr Thr Arg Gln Pro Leu Leu Ser His Lys
```

-continued

```
            625                 630                 635                 640
Lys Gly Glu Gln Pro Leu Leu Leu Thr Asn Ala Glu Leu Lys Asp Tyr
                    645                 650                 655

Ser Gly Leu His Asp Val Ala Val Gly Asp Gly Leu Ser Glu Gly
                660                 665                 670

Ala Thr Ala Asn Gly Met Lys Ser Met
                675                 680

<210> SEQ ID NO 12
<211> LENGTH: 371
<212> TYPE: PRT
<213> ORGANISM: Homo sapien

<400> SEQUENCE: 12

Met Ile Thr Met Val Ala Ser Phe Val Ala Met Ala Gly Gln Phe Leu
 1               5                  10                  15

Met Pro Gly Leu Ala Ala Leu Cys Arg Asp Trp Gln Val Leu Gln Ala
                20                  25                  30

Leu Ile Ile Cys Pro Phe Leu Leu Met Leu Leu Tyr Trp Ser Ile Phe
            35                  40                  45

Pro Glu Ser Leu Arg Trp Leu Met Ala Thr Gln Gln Phe Glu Ser Ala
        50                  55                  60

Lys Lys Leu Ile Leu Tyr Leu Thr Gln Lys Asn Cys Val Ser Pro Glu
65                  70                  75                  80

Ser Asp Ile Lys Gly Val Met Pro Glu Leu Glu Lys Glu Leu Ser Arg
                85                  90                  95

Arg Pro Lys Lys Val Cys Ile Val Lys Val Val Gly Thr Arg Asn Leu
                100                 105                 110

Trp Lys Asn Ile Val Val Leu Cys Val Asn Ser Leu Thr Gly Tyr Gly
            115                 120                 125

Ile His His Cys Phe Ala Arg Ser Met Met Gly His Glu Val Lys Val
        130                 135                 140

Pro Leu Leu Glu Asn Phe Tyr Ala Asp Tyr Tyr Thr Thr Ala Ser Ile
145                 150                 155                 160

Ala Leu Val Ser Cys Leu Ala Met Cys Val Val Arg Phe Leu Gly
                165                 170                 175

Arg Arg Gly Gly Leu Leu Phe Met Ile Leu Thr Ala Leu Ala Ser
                180                 185                 190

Leu Leu Gln Leu Gly Leu Leu Asn Leu Ile Gly Lys Tyr Ser Gln His
            195                 200                 205

Pro Asp Ser Gly Met Ser Asp Ser Val Lys Asp Lys Phe Ser Ile Ala
        210                 215                 220

Phe Ser Ile Val Gly Met Phe Ala Ser His Ala Val Gly Ser Leu Ser
225                 230                 235                 240

Val Phe Phe Cys Ala Glu Ile Thr Pro Thr Val Ile Arg Cys Gly Gly
                245                 250                 255

Leu Gly Leu Val Leu Ala Ser Ala Gln Phe Gly Met Leu Thr Ala Pro
                260                 265                 270

Ile Ile Glu Leu His Asn Gln Lys Gly Tyr Phe Leu His His Ile Ile
            275                 280                 285

Phe Ala Cys Cys Thr Leu Ile Cys Ile Ile Cys Ile Leu Leu Leu Pro
        290                 295                 300

Glu Ser Arg Asp Gln Asn Leu Pro Glu Asn Ile Ala Asn Gly Glu His
305                 310                 315                 320

Tyr Thr Arg Gln Pro Leu Leu Ser His Lys Lys Gly Glu Gln Pro Leu
```

-continued

```
                    325                 330                 335
Leu Leu Thr Asn Ala Glu Leu Lys Asp Tyr Ser Gly Leu His Asp Val
            340                 345                 350

Ala Ala Val Gly Asp Gly Leu Ser Glu Gly Ala Thr Ala Asn Gly Met
            355                 360                 365

Lys Gly Met
        370
```